(12) United States Patent
Grüne et al.

(10) Patent No.: US 10,358,399 B2
(45) Date of Patent: Jul. 23, 2019

(54) PROCESS FOR PREPARING 1,3-BUTADIENE FROM N-BUTENES BY OXIDATIVE DEHYDROGENATION

(71) Applicants: BASF SE, Ludwigshafen (DE); Linde AG, Munich (DE)

(72) Inventors: Philipp Grüne, Mannheim (DE); Stephan Deublein, Harthausen (DE); Christian Walsdorff, Ludwigshafen (DE); Jan Pablo Josch, Neustadt (DE); Rainer Rahm, Kirchheim (DE); Hendrik Reyneke, Munich (DE); Anton Wellenhofer, Hohenschaeftlarn (DE); Ulrike Wenning, Pullach (DE); Christine Toegel, Neubiberg (DE); Heinz Boelt, Wolfratshausen (DE)

(73) Assignees: BASF SE, Ludwigshafen am Rhein (DE); Linde AG, Munich (DE)

( * ) Notice: Subject to any disclaimer, the term of this patent is extended or adjusted under 35 U.S.C. 154(b) by 0 days.

(21) Appl. No.: 15/523,862

(22) PCT Filed: Nov. 2, 2015

(86) PCT No.: PCT/EP2015/075422
§ 371 (c)(1),
(2) Date: May 2, 2017

(87) PCT Pub. No.: WO2016/071268
PCT Pub. Date: May 12, 2016

(65) Prior Publication Data
US 2017/0334809 A1 Nov. 23, 2017

(30) Foreign Application Priority Data
Nov. 3, 2014 (EP) .................................. 14191547

(51) Int. Cl.
*C07C 5/48* (2006.01)
*B01D 3/40* (2006.01)
(Continued)

(52) U.S. Cl.
CPC ................ *C07C 5/48* (2013.01); *C07C 7/005* (2013.01); *C07C 7/04* (2013.01); *C07C 7/08* (2013.01);
(Continued)

(58) Field of Classification Search
CPC .. C07C 5/333; C07C 7/05; C07C 5/48; C07C 5/327
See application file for complete search history.

(56) References Cited

U.S. PATENT DOCUMENTS

| | | |
|---|---|---|
| 3,911,039 A | 10/1975 | Grasselli et al. |
| 3,914,332 A | 10/1975 | Dickason |

(Continued)

FOREIGN PATENT DOCUMENTS

| | | |
|---|---|---|
| CN | 101492334 B | 11/2012 |
| CN | 101492335 B | 7/2013 |

(Continued)

OTHER PUBLICATIONS

"Maleic Anhydride (table of contents)", A Report by Nexant, 2013, pp. 1-10.
(Continued)

*Primary Examiner* — Youngsul Jeong
(74) *Attorney, Agent, or Firm* — Drinker Biddle & Reath LLP

(57) ABSTRACT

A process for preparing butadiene from n-butenes, comprising the steps of:
A) providing an input gas stream comprising n-butenes;
(Continued)

B) feeding the input gas stream comprising n-butenes and a gas containing at least oxygen into at least one oxidative dehydrogenation zone and oxidatively dehydrogenating n-butenes to butadiene, giving a product gas stream;

Ca) cooling the product gas stream by contacting with a circulating cooling medium in at least one cooling zone;

Cb) compressing the cooled product gas stream in at least one compression stage, giving at least one aqueous condensate stream c1 and one gas stream c2;

D) removing uncondensable and low-boiling gas constituents comprising oxygen and low-boiling hydrocarbons as gas stream d2 from the gas stream c2 by absorbing the $C_4$ hydrocarbons in an absorbent, giving an absorbent stream laden with $C_4$ hydrocarbons and the gas stream d2, and then desorbing the $C_4$ hydrocarbons from the laden absorbent stream, giving a $C_4$ product gas stream d1;

E) separating the $C_4$ product stream d1 by extractive distillation;

F) distilling the stream e1 into a stream f1 consisting essentially of the selective solvent and a stream f2 comprising butadiene;

G) removing a portion of the aqueous phase of the cooling medium which circulates in step Ca) as aqueous purge stream g;

H) distillatively separating the aqueous purge stream g into a fraction h1 and a fraction h2 depleted of organic constituents.

16 Claims, 6 Drawing Sheets

(51) Int. Cl.
  *C07C 7/05* (2006.01)
  *C07C 7/04* (2006.01)
  *C07C 7/08* (2006.01)
  *C07C 7/11* (2006.01)
  *C07C 7/00* (2006.01)
  *C07C 11/167* (2006.01)

(52) U.S. Cl.
  CPC .............. *C07C 7/11* (2013.01); *C07C 11/167* (2013.01); *C07C 2523/31* (2013.01); *C07C 2523/843* (2013.01); *C07C 2523/847* (2013.01)

(56) References Cited

U.S. PATENT DOCUMENTS

| | | |
|---|---|---|
| 3,932,551 A | 1/1976 | Grasselli et al. |
| 3,956,181 A | 5/1976 | Grasselli et al. |
| 3,959,400 A | 5/1976 | Lucki |
| 3,965,126 A | 6/1976 | Wirth et al. |
| 4,162,234 A | 7/1979 | Grasselli et al. |
| 4,219,388 A | 8/1980 | Heller et al. |
| 4,336,409 A | 6/1982 | Yamamoto et al. |
| 4,397,771 A | 8/1983 | Grasselli et al. |
| 4,423,281 A | 12/1983 | Yamamoto et al. |
| 4,424,141 A | 1/1984 | Grasselli et al. |
| 4,504,692 A | 3/1985 | Arakawa et al. |
| 4,511,750 A | 4/1985 | Miller |
| 4,547,615 A | 10/1985 | Yamamoto |
| 4,961,827 A | 10/1990 | Zimmerling et al. |
| 5,324,419 A | 6/1994 | Muldowney |
| 5,849,972 A | 12/1998 | Vicari et al. |
| 6,852,898 B2 | 2/2005 | Schulz et al. |
| 6,913,742 B2 * | 7/2005 | Okajima .................. C01D 3/14 423/499.4 |
| 7,259,285 B1 | 8/2007 | Walter et al. |
| 7,932,428 B2 | 4/2011 | Rix et al. |
| 9,255,041 B2 | 2/2016 | Yano et al. |
| 2005/0288471 A1 | 12/2005 | Bitterlich et al. |
| 2007/0191212 A1 | 8/2007 | Schubert et al. |
| 2008/0045766 A1 | 2/2008 | Schubert et al. |
| 2008/0200745 A1 | 8/2008 | Sigl et al. |
| 2009/0030251 A1 | 1/2009 | Senetar et al. |
| 2012/0130137 A1 | 5/2012 | Orita et al. |
| 2013/0281748 A1 | 10/2013 | Cha et al. |
| 2014/0200381 A1 * | 7/2014 | Josch ...................... C07C 7/05 585/621 |
| 2015/0126788 A1 * | 5/2015 | Takagaki .................. C07C 7/10 585/326 |
| 2016/0152531 A1 | 6/2016 | Walsdorff et al. |
| 2016/0347686 A1 | 12/2016 | Grune et al. |
| 2016/0355450 A1 | 12/2016 | Grune et al. |
| 2017/0233313 A1 | 8/2017 | Grune et al. |
| 2018/0002254 A1 | 1/2018 | Josch et al. |

FOREIGN PATENT DOCUMENTS

| | | |
|---|---|---|
| DE | 2440329 A1 | 3/1975 |
| DE | 2447825 A1 | 8/1975 |
| DE | 2530959 A1 | 2/1976 |
| DE | 2600128 A1 | 7/1976 |
| DE | 4339713 A1 | 5/1995 |
| DE | 102004009803 A1 | 9/2005 |
| DE | 102004009804 A1 | 9/2005 |
| DE | 102004009805 A1 | 9/2005 |
| EP | 272970 | 6/1988 |
| EP | 2711350 A1 | 3/2014 |
| FR | 2641477 A1 | 7/1990 |
| JP | 2011001341 A | 1/2011 |
| JP | 2011006381 A | 1/2011 |
| JP | 2013119530 A | 6/2013 |
| JP | 2013177380 A | 9/2013 |
| KR | 20130036467 A | 4/2013 |
| KR | 20130036468 A | 4/2013 |
| KR | 20130045259 A | 5/2013 |
| WO | WO-9925668 A1 | 5/1999 |
| WO | WO-200137989 A2 | 5/2001 |
| WO | WO-200172670 A1 | 10/2001 |
| WO | WO-2004039757 A2 | 5/2004 |
| WO | WO-2006089956 A2 | 8/2006 |
| WO | WO-2012157495 A1 | 11/2012 |
| WO | WO-2013098760 A1 | 7/2013 |
| WO | WO-2013106039 A1 | 7/2013 |
| WO | WO-2014111406 A1 | 7/2014 |
| WO | WO-2014160825 A1 | 10/2014 |
| WO | WO-2015055613 A1 | 4/2015 |

OTHER PUBLICATIONS

"Ullmanns Encyklopädie der technischen Chemie", 4., neubearbeitete und erweiterte Auflage Band 9, 1975, vol. 9, 4th Ed., pp. 1-18.

Jung, J.C., et al., "Catalytic performance of bismuth molybdate catalysts in the oxidative dehydrogenation of C4 raffinate-3 to 1,3-butadiene", Applied Catalysis A: General, 2007, vol. 317, pp. 244-249.

Jung, J.C., et al., "Production of 1,3-Butadiene From C4 Raffinate-3 Through Oxidative Dehydrogenation of n--Butene Over Bismuth Molybdate Catalysts", Catal. Surv. Asia, 2009, vol. 13, pp. 78-93.

Kraume, M., et al., "Continuous Mixing of Fluids (Table of Contents)", Ullmann's Encyclopedia of Industrial Chemistry, Wiley-VCH, 2012, obtained from http://onlinelibrary.wiley.com/doi/10.1002/14356007.

Pahl, M., et al., "Einsatz und Auslegung statischer Mischer", Chem. Ing. Tech., 1979, vol. 51, No. 5, pp. 347-364.

Streiff, F., "Statische Mischer mit großer Anpassungsfähigkeit", Chem. Ing. Tech., 1980, vol. 52, No. 6, pp. 520-522.

Volkamer, K., et. al., "Entwicklungsarbeiten am Butadien-verfahren der BASF", 1981, vol. 34, No. 8, pp. 343-346.

International Preliminary Examination Report for PCT/EP2015/075422 dated Oct. 21, 2016.

(56) References Cited

OTHER PUBLICATIONS

International Search Report for PCT/EP2015/075422 dated Jan. 26, 2016.
International Search Report for PCT/EP2015/076018 dated Jan. 25, 2016.
Written Opinion of the International Searching Authority for PCT/EP2015/076018 dated Jan. 26, 2016.

* cited by examiner

PROCESS FOR PREPARING 1,3-BUTADIENE FROM N-BUTENES BY OXIDATIVE DEHYDROGENATION

CROSS-REFERENCE TO RELATED APPLICATIONS

This application is a national stage application (under 35 U.S.C. § 371) of PCT/EP2015/075422, filed Nov. 2, 2015, which claims benefit of European Application No. 14191547.0, filed Nov. 3, 2014, both of which are incorporated herein by reference in their entirety.

The invention relates to a process for preparing 1,3-butadiene from n-butenes by oxidative dehydrogenation (ODH).

BACKGROUND OF THE INVENTION

Butadiene is an important base chemical and is used, for example, for production of synthetic rubbers (butadiene homopolymers, styrene-butadiene rubber or nitrile rubber) or for production of thermoplastic terpolymers (acrylonitrile-butadiene-styrene copolymers). Butadiene is also converted to sulfolane, chloroprene and 1,4-hexamethytenediamine (via 1,4-dichlorobutene and adiponitrile). Through dimerization of butadiene, it is also possible to obtain vinylcyclohexene, which can be dehydrogenated to styrene.

Butadiene (1,3-butadiene) can be prepared by thermal cracking (steamcracking) of saturated hydrocarbons, typically proceeding from naphtha as the raw material. The steamcracking of naphtha affords a hydrocarbon mixture of methane, ethane, ethene, acetylene, propane, propene, propyne, allene, butanes, butenes, 1,2-butadiene and 1,3-butadiene, butynes, methylallene, and $C_5$ and higher hydrocarbons.

Butadiene can also be obtained by the oxidative dehydrogenation of n-butenes (1-butene and/or 2-butene). The input gas utilized for the oxidative dehydrogenation (oxydehydrogenation, ODH) of n-butenes to butadiene may be any desired mixture comprising n-butenes. For example, it is possible to use a fraction which comprises n-butenes (1-butene and/or 2-butene) as the main constituent and has been obtained from the $C_4$ fraction from a naphtha cracker by removing butadiene and isobutene. In addition, it is also possible to use gas mixtures which comprise 1-butene, cis-2-butene, trans-2-butene or mixtures thereof and have been obtained by dimerization of ethylene as input gas. In addition, input gases used may be gas mixtures which comprise n-butenes and have been obtained by catalytic fluidized bed cracking (fluid catalytic cracking, FCC).

Processes for oxidative dehydrogenation of butenes to butadiene are known in principle.

US 2012/0130137 A1, for example, describes a process of this kind using catalysts comprising oxides of molybdenum, bismuth and generally further metals. For the lasting activity of such catalysts for the oxidative dehydrogenation, a critical minimum level of partial oxygen pressure is required in the gas atmosphere in order to avoid an excessive reduction and hence a loss of performance of the catalysts. For this reason, it is generally also not possible to work with a stoichiometric oxygen input or complete oxygen conversion in the oxydehydrogenation reactor (ODH reactor). US 2012/0130137 describes, for example, an oxygen content of 2.5% to 8% by volume in the starting gas.

The need for an oxygen excess for such catalyst systems is common knowledge and reflected in the process conditions when catalysts of this kind are used. Representative examples include the comparatively recent studies by Jung et al. (Catal. Surv. Asia 2009, 13, 78-93; DOI 10.1007/s10563-009-9069-5 and Applied Catalysis A: General 2007, 317, 244-249; DOI 10.1016/j.apcata.2006.10.021).

JP-A 2011-006381 to Mitsubishi addresses the risk of peroxide formation in the workup section of a process for preparing conjugated alkadienes. As a solution, the addition of polymerization inhibitors to the absorption solutions for the process gases and the setting of a maximum peroxide content of 100 ppm by weight by heating the absorption solutions is described. However, there is no information as to avoidance or monitoring of peroxides in upstream process steps. A particularly critical aspect is the step of cooling the ODH reactor output with a water quench. Organic peroxides formed are barely soluble in water, and so they are deposited and can accumulate in the apparatus in solid or liquid form, instead of being discharged with the aqueous purge stream. At the same time, the temperature of the water quench is not so high that sufficiently high and constant breakdown of the peroxides formed can be assumed.

The catalytic oxidative dehydrogenation can form high-boiling secondary components, for example maleic anhydride, phthalic anhydride, benzaldehyde, benzoic acid, ethylbenzene, styrene, fluorenone, anthraquinone and others. Deposits of these components can lead to blockages and to a rise in the pressure drop in the reactor or beyond the reactor in the workup area, and can thus disrupt regulated operation. Deposits of the high-boiling secondary components mentioned can also impair the function of heat exchangers or damage moving apparatuses such as compressors. Steam-volatile compounds such as fluorenone can get through a quench apparatus operated with water and precipitate beyond it in the gas discharge lines. In principle, there is therefore also the risk that solid deposits will get into downstream apparatus parts, for example compressors, and cause damage there.

US 2012/0130137 A1 paragraph [0122] also refers to the problem of high-boiling by-products. Particular mention is made of phthalic anhydride, anthraquinone and fluorenone, which are said to be present typically in concentrations of 0.001% to 0.10% by volume in the product gas. US 2012/0130137 A1 paragraphs [0124]-[0126] recommends cooling the hot reactor discharge gases directly, by contact with a cooling liquid (quench tower), at first to typically 5-100° C. The cooling liquids mentioned are water or aqueous alkali solutions. There is explicit mention of the problem of blockages in the quench by high boilers from the product gas or by polymerization products of high-boiling by-products from the product gas, and for this reason it is said to be advantageous that high-boiling by-products are entrained as little as possible from the reaction section to the cooling section (quench).

JP-A 2011-001341 describes a two-stage cooling operation for a process for oxidative dehydrogenation of alkenes to conjugated alkadienes. This involves first cooling the product discharge gas from the oxidative dehydrogenation to a temperature between 300 and 221° C. and then cooling it further to a temperature between 99 and 21° C. Paragraphs [0066] ff. state that the temperature between 300 and 221° C. is preferably established using heat exchangers, but a portion of the high boilers could also precipitate out of the product gas in these heat exchangers. JP-A 2011-001341 therefore describes occasional washing of deposits out of the heat exchangers with organic or aqueous solvents. Solvents described are, for example, aromatic hydrocarbons such as toluene or xylene, or an alkaline aqueous solvent, for example the aqueous solution of sodium hydroxide. In order to avoid excessive frequency of interruption of the process to clean the heat exchanger, JP-A 2011-001341 describes a setup having two heat exchangers arranged in parallel, which are each alternately operated or rinsed (called NB operation mode).

JP-A 2013-119530 describes a quench in which an ODH product gas is cooled by direct contact with water. Paragraph 7 addresses the problem that the product gas entrains solid constituents and that these can prevent stable operation. Solid constituents were even said to be found in the offgas of the quench column. Paragraph 41 asserts that these constituents consist mainly of isophthalic acid and terephthalic acid. Even if the amount in the offgas is small, it is said that filters, for example, could be covered very rapidly. According to this application, the solid constituents are eliminated as far as possible from the product gas through suitable choice of internals and of the volume flow ratio of coolant and gas stream. However, the application does not give any information as to how blockage of the coolant circuit can be avoided.

JP-A 2013-177380 describes, in paragraph 60, possible coolants used in the product gas quench. Cooling liquids mentioned in general terms are saturated hydrocarbons, unsaturated hydrocarbons, aromatic hydrocarbons, esters, ethers, aldehydes, ketones, amines, acids, water and mixtures thereof. The preferred coolant is water. Paragraph 62 describes the supply and removal of water as coolant: according to this, at least a portion of the water which has been discharged from the bottom of the cooling tower can be fed back to a middle stage and/or to the top of the cooling tower. The water withdrawn from the bottom may comprise solids. For the removal thereof, the document suggests standard processes, for example the use of a screen. Paragraphs 63 and 64 mention, as by-products which condense out in the coolant, oxygenous organic compounds such as aldehydes, ketones, carboxylic acid, unsaturated aldehydes, unsaturated carboxylic acid, and polymers having the compounds mentioned as a structural unit.

According to WO 2012/157495, the aqueous solution of an organic amine is used as coolant in the product gas quench of an oxydehydrogenation. Paragraph 6 describes the problem of blockage of lines by solids. Accordingly, it has been found that high-boiling by-products such as organic acids, aldehydes and ketones condense when the reaction product gas is quenched with cooling water and flow along with the flow of the reaction product gas, which results in blockage of lines and endangerment of the continuous operation of the plant.

Effective removal of the components is said to be achieved through use of an aqueous solution of an organic amine and of a preferably aromatic solvent. However, the two coolants are used in separate regions of the cooling tower. Thus, paragraph 35 states that a first quench tower is used for the scrubbing of the reaction product gas with the aqueous solution of organic amine, and a second quench tower for the purification of the reaction product gas with the aromatic solvent. Paragraph 38 says that the spent aqueous solution of the organic amine and the spent aromatic solvent can be incinerated.

KR 2013-0036467 and KR 2013-0036468 describe the use of a mixture of water and a water-miscible organic solvent as coolant in a product gas quench of an oxydehydrogenation. Owing to water miscibility, the workup and regeneration of the organic solvent is very energy-intensive and is disadvantageous from an economic point of view.

U.S. Pat. Nos. 3,965,126, 4,219,388 and 4,961,827 describe the removal and purification of maleic anhydride from maleic acid-containing scrubbing solutions. Such scrubbing solutions are obtained, for example, in the production of phthalic anhydride. The recovery of maleic anhydride from phthalic anhydride processes is described, for example, in the PERP Report 2013 May "Maleic anhydride" from Nexant (published December 2013) in chapter 3.5.

DETAILED DESCRIPTION OF THE INVENTION

Figure 1:
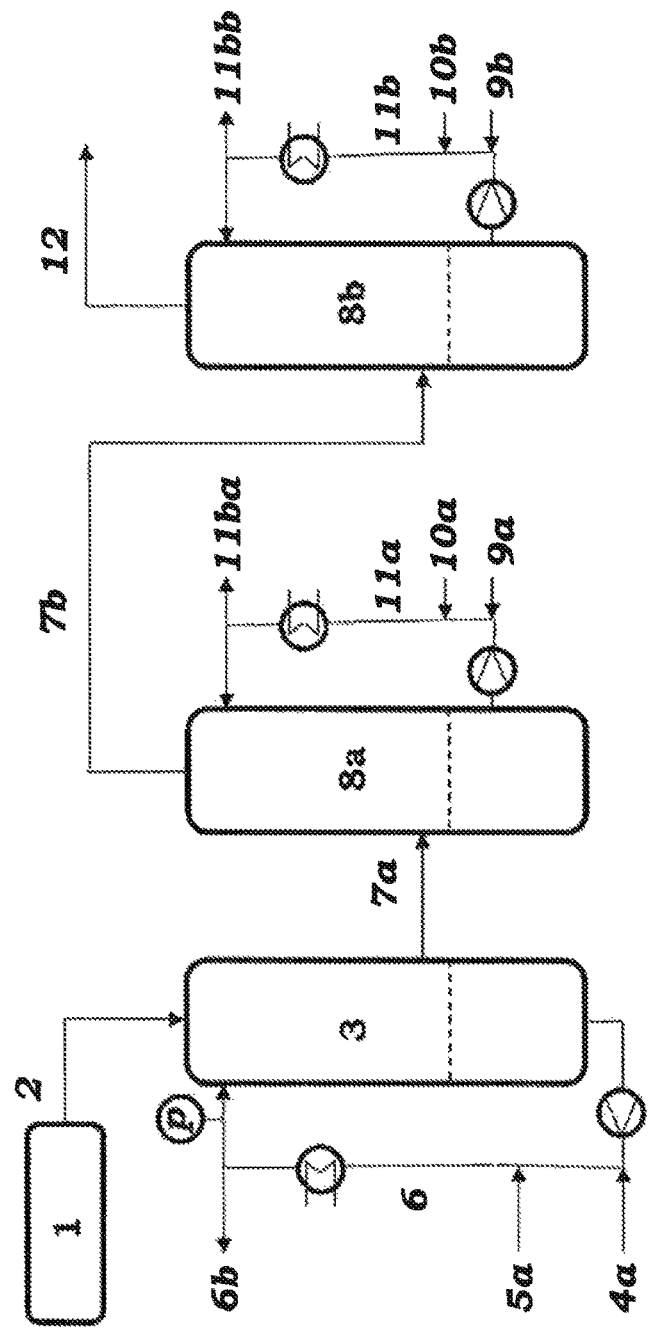
FIG. 1 is a schematic diagram of the reaction process with second and third quench stage.

It is an object of the present invention to provide a process which remedies the abovementioned disadvantages of known processes, and which is particularly economically viable.

The object is achieved by a process for preparing butadiene from n-butenes, comprising the steps of:

A) providing an input gas stream a comprising n-butenes;
B) feeding the input gas stream a comprising n-butenes and at least one oxygenous gas into at least one oxidative dehydrogenation zone and oxidatively dehydrogenating n-butenes to butadiene, giving a product gas stream b comprising butadiene, unconverted n-butenes, water vapor, oxygen, low-boiling hydrocarbons and high-boiling secondary components, with or without carbon oxides and with or without inert gases;
Ca) cooling the product gas stream b by contacting with a circulating cooling medium in at least one cooling zone, the cooling medium being at least partly recycled in at least one cooling zone and having an aqueous phase and an organic phase comprising an organic solvent;
Cb) compressing the cooled product gas stream b which may have been depleted of high-boiling secondary components in at least one compression stage, giving at least one aqueous condensate stream c1 and one gas stream c2 comprising butadiene, n-butenes, water vapor, oxygen and low-boiling hydrocarbons, with or without carbon oxides and with or without inert gases;
D) removing uncondensable and low-boiling gas constituents comprising oxygen and low-boiling hydrocarbons, with or without carbon oxides and with or without inert gases, as gas stream d2 from the gas stream c2 by absorbing the $C_4$ hydrocarbons comprising butadiene and n-butenes in an absorbent, giving an absorbent stream laden with $C_4$ hydrocarbons and the gas stream d2, and then desorbing the $C_4$ hydrocarbons from the laden absorbent stream, giving a $C_4$ product gas stream d1;
E) separating the $C_4$ product stream d1 by extractive distillation with a butadiene-selective solvent into a stream e1 comprising butadiene and the selective solvent and a stream e2 comprising n-butenes;

F) distilling the stream e1 comprising butadiene and the selective solvent into a stream f1 consisting essentially of the selective solvent and a stream f2 comprising butadiene;

which comprises

G) removing a portion of the aqueous phase of the cooling medium which circulates in step Ca) and has an aqueous phase and an organic phase as aqueous purge stream g;

H) separating the aqueous purge stream g by distillation into a fraction h1) enriched in organic constituents and a fraction h2) depleted of organic constituents.

In one embodiment of the invention, in a further step I):

I) at least one fraction i1 is obtained as product of value from the stream h1.

In a further embodiment of the invention, in a further step J):

J) at least one fraction j1 from the stream h1 is sent to a thermal utilization.

In a preferred embodiment of the present invention,

I) at least one fraction i1 is obtained as product of value from the stream h1, and J) at least one fraction j1 from the stream h1 is sent to a thermal utilization.

In a particularly preferred embodiment of the present invention,

I) at least one fraction i1 is obtained as product of value from the stream h1, and J) removal of the at least one fraction i1 leaves a fraction j1 which is sent to a thermal utilization.

According to the invention, a process in which deposits resulting from high-boiling organic secondary constituents in the apparatuses connected downstream of the ODH can be avoided is provided. It is a feature of the process that it is not easy for blockages by solids dispersed in the coolant to occur in the coolant circuit (quench circuit), especially in the nozzles through which the coolant is fed into the cooling zone, and hence stable continuous quench circulation can be assured. It is a further feature of the process that the possible enrichment of organic peroxides can be avoided.

The process according to the invention is particularly economically viable, since the wastewater which has been worked up, i.e. the fraction h2 depleted of organic constituents, can be recycled into the process as process water, for example into stage Ca), or can be sent to the biological stage of a water treatment plant for further workup. The fraction h1 enriched in organic constituents can be incinerated, for example, for the purpose of heat recovery. The process can be operated in such a way that the heat generated by the incineration of the organic constituents is sufficient for virtually complete distillative removal of the organic constituents from the wastewater stream (purge stream g). Finally, it is possible to remove organic constituents of the fraction h1 in suitable additional process stages and to obtain them as products of value.

Continuous operation of the quench circuit is possible for longer when the circuit is operated with two mutually immiscible coolants. In addition, continuous operation is possible for a particularly long period when the two immiscible solvents are in a particular ratio on entry into the quench column. In addition, continuous operation is possible for a particularly long period when the two immiscible solvents are dispersed intimately with one another on entry into the quench column.

The phase ratio, i.e. the ratio of the mass of the aqueous phase to the mass of the organic phase of the cooling medium on entry into the first direct cooling stage (quench stage) prior to contacting is determined via the flow rates of the aqueous and organic coolants added to the coolant circuit, the flow rate of water vapor present in the product gas stream, the flow rates of water vapor and organic coolant which leave the cooling stage, and the flow rates of the aqueous and organic phases which are withdrawn from the coolant circuit as output stream (purge). The phase ratio is generally greater than or equal to 0.13:1, preferably greater than or equal to 0.15:1, more preferably greater than or equal to 0.18:1, in particular greater than or equal to 0.2:1 and especially greater than or equal to 0.3:1, and less than or equal to 100:1, especially greater than or equal to 0.3:1 and less than or equal to 100:1, preferably less than or equal to 10:1, more preferably less than or equal to 2:1, especially less than or equal to 1:1. Preferred ranges of the phase ratio are 0.15:1 to 10:1, more preferably 0.15:1 to 5:1, and in particular 0.18:1 to 2:1.

The organic constituents dissolved in the aqueous purge stream g are the organic solvent used in the biphasic cooling medium and high-boiling secondary constituents formed in the oxydehydrogenation reaction. Organic solvents used with preference are aromatic hydrocarbons, more preferably toluene, o-xylene, m-xylene, p-xylene, mesitylene, mono-, di- and triethylbenzene, mono-, di- and triisopropylbenzene and mixtures thereof. Particular preference is given to mesitylene. High-boiling secondary constituents are, for example, formaldehyde, formic acid, acetaldehyde, acetic acid, acrolein, acrylic acid, propionaldehyde, propionic acid, methacrolein, methacrylic acid, crotonaldehyde, crotonic acid, fumaric acid, maleic acid, maleic anhydride, benzaldehyde, benzoic acid, phthalic anhydride and phthalic acid.

In general, 0.1% to 80%, preferably 0.5% to 40%, of the aqueous phase of the overall coolant which circulates in the quench is removed per hour as purge stream g. The smaller the proportion of the aqueous phase removed as purge stream g in the overall aqueous phase, the greater the enrichment of the aqueous phase with organic constituents. In general, the content of the dissolved organic constituents in the aqueous phase is 1% to 60% by weight, preferably 5% to 45% by weight.

In general, the purge stream g of the aqueous phase of the coolant is 0.5% to 100%, preferably 1% to 75%, of the mass flow of the butenes supplied to the reactor. The smaller the proportion of the aqueous phase removed as purge stream g in the overall aqueous phase, the greater the enrichment of the aqueous phase with organic constituents. The content of the dissolved organic constituents in the aqueous phase is typically 1% to 70% by weight, preferably 5% to 50% by weight. The total organic carbon (TOC) to DIN EN 1484 is typically between 0.5% and 50% by weight, preferably between 2% and 40% by weight.

In a preferred embodiment, the dewatering step H) is conducted by distillation or rectification in such a way that at least 70% by weight of the organic constituents present in the aqueous purge stream g) is removed by distillation from the purge stream. Preferably at least 80% by weight, more preferably at least 90% by weight, of the organic constituents is removed. The concentration of the organic constituents in the distillate stream h1 which forms is at least 50% by weight, more preferably at least 70% by weight. The proportion of the organic constituents in the aqueous fraction h2 is not more than 50% by weight, more preferably not more than 30% by weight.

In general, the distillation is conducted in an evaporator system with a downstream condenser system (embodiment 1). An evaporator system consists of one or more parallel and/or series-operated evaporators, preference being given to the use of one evaporator. A condenser system consists of one or more parallel and/or series-operated condensers, preference being given to the use of not more than two series-connected condensers, particular preference to the use of one condenser. The individual constituents for workup may be interspersed by intermediate vessels.

The distillation is generally conducted at a pressure in the individual apparatuses of 0.006 bar to 5 bar. The pressure is preferably between 0.05 bar and 1 bar. More preferably, the evaporator system is coupled to the condenser system, such that only the pressure of the condenser system is set and kept constant. The pressure in the evaporator system results from the pressure of the condenser system and the pressure drop thereof. The evaporator temperature $T_{evap}$ is between 10° C. and 200° C., more preferably between 40° C. and 130° C.

Evaporation can be accomplished using any evaporators familiar to those skilled in the art, preference being given to the use of falling-film evaporators or thin-film evaporators (for example of the Sambay type or of the Luwa type with rotating internals). It has been found that, when these two evaporator types are used, precipitation of organic solids in the phase h1 enriched in organic constituents can be reduced. A preferable alternative is a short-path evaporator.

The condensation temperature in the condenser system is generally between 10° C. and 200° C., more preferably between 40° C. and 130° C. In general, it is possible to use any condensers known to those skilled in the art, preference being given to an air cooler or a tubular cooler. The cooling medium used is preferably air or water.

In an alternative embodiment, the distillation is conducted in an evaporator system, a column and a condenser system. An evaporator system and a condenser system are defined as detailed above. The column is filled with internals, preferably with unstructured packings. The system is characterized by the addition of liquid in the upper portion of the column. The liquid preferably includes all the condensable components of the gaseous stream; the deviation in the composition of the liquid is preferably from +20% by weight to −20% by weight. More preferably, the condensed liquid in the gas stream from the column is recycled in portions.

The operating pressure and the operating temperatures in the individual apparatuses and the individual apparatuses used are as described above in connection with embodiment 1, as are the preferred operating pressure range and operating temperature range and the preferred apparatuses. The coupling of all the apparatuses is particularly preferred in the alternative system too, the pressure of the overall apparatus being set in the condenser system. The pressure in the column and in the evaporator results from the pressure drops in the individual apparatuses.

The separating performance of the column is between 0 and 50 plates, preferably between 0 and 20 plates.

The fraction h1 enriched in organic constituents comprises generally 0.1% to 30% by weight of water, 0.001% to 20% by weight of the organic solvent and 50% to 99.99% by weight of high-boiling organic secondary constituents. It has been found that the proportion of maleic acid and maleic anhydride in the high-boiling organic secondary constituents is surprisingly high. Thus, this proportion is generally 10% to 99% by weight, preferably 20% to 80% by weight, based on the total amount of high-boiling organic secondary constituents.

In a further preferred embodiment, in a further distillation step I), maleic anhydride is removed by distillation as product of value from the fraction h1 enriched in organic constituents.

The distillation is effected by the principle of rectification. All the high-boiling components are enriched and removed in the bottom of the column. The concentration of the high boilers in this case is between 50% by weight and 100% by weight, preferably between 70% by weight and 100% by weight. All the low-boiling components are enriched at the top of the column and removed from the product of value. The product of value is obtained in concentrated form, preferably via a side draw from the column. The concentration of the product of value is between 50% by weight and 100% by weight, preferably between 70% by weight and 100% by weight, more preferably between 90% by weight and 100% by weight. Alternatively, the product can also be obtained via the tops discharge or the bottoms discharge from the column, contaminated by the low- or high-boiling components.

Internals used in the column may be any internals known to those skilled in the art. Preference is given to using trays in the stripping section of the column. The number of trays is between 1 and 30 trays. It has been found that use of the trays in the stripping section can reduce precipitation of organic solids within the column. In the rectifying section of the column, preference is given to using structured packings, which are characterized by a low pressure drop combined with high separating performance. Preferably, the rectifying section of the column consists of between 0.1 m and 30 m of packing installed in the form of one or more beds. Any of the packing types known to those skilled in the art can be used in the rectifying section.

The rectification to obtain maleic anhydride is generally conducted at a column top pressure between 1 mbar and 1 bar, preferably between 5 mbar and 500 mbar.

Because of the corrosivity of organic acids and anhydrides, especially of maleic acid and maleic anhydride and of further organic substances, materials of adequate stability for the above-described workup should be used, for example high-alloy stainless steel or titanium.

In a preferred embodiment, the fraction j1 from h1 is sent to an incineration and the heat which arises in the incineration is utilized for operation of a distillation column or of an evaporator in which the aqueous purge stream g is distilled. More preferably, in a further distillation step I), maleic anhydride is first removed by distillation as at least one fraction i1 from the fraction h1 enriched in organic constituents, in which case the remaining fraction depleted of maleic anhydride is subsequently incinerated as fraction j1.

The incineration is effected in a standard incineration furnace. The hot vapors which arise are preferably utilized to drive a turbine with generation of power or to raise steam using an indirect heat transferrer. In a preferred embodiment, the vapor is produced at a temperature at least 5° C. above the water evaporation temperature $T_{evap}$. In a particularly preferred embodiment, steam is raised. In a preferred variant, the indirect heat transferrer is a heat carrier oil which can be heated to up to 300° C. or higher temperatures and which provides heat for the distillation of the aqueous purge stream g.

It may also be advantageous to limit the flue gas temperatures, i.e. the temperature of the offgas in the incineration, to 500° C. for 400° C., for example, in order to reduce the stress on the materials used. The incineration is generally conducted under optimized conditions with a view of a good incineration outcome. These include, for example, the setting of an optimal air/fuel ratio or suitable atomization of the fuel.

In a particularly preferred embodiment, the portion of the aqueous phase of the cooling medium which is removed in step G) is such that the heat which arises in the incineration of the fraction h1 enriched in organic constituents is sufficient to operate the distillation column or the evaporator. In this embodiment of the process, the portion of the aqueous phase of the cooling medium which is removed as purge stream in step G) is preferably 1% to 20% by weight, more preferably 2% to 15% by weight, of the aqueous phase of the coolant present in the quench as inventory. In addition, the purge stream g) of the aqueous phase of the coolant is 2% to 40%, preferably 4% to 35%, of the mass flow of the butenes supplied to the reactor. This affords an aqueous purge stream g particularly highly enriched in organic constituents. In this embodiment, the content of the dissolved organic constituents in the aqueous phase is 8% to 40% by weight, preferably 12% to 35% by weight.

In a further preferred embodiment, a portion of the aqueous fraction h2 depleted of organic constituents is fed as aqueous coolant back to the circulating cooling medium in stage Ca). This portion may be more than 30%, preferably more than 50%, of fraction h2.

In a further embodiment of the invention, the stream h1 is subjected to a thermal treatment, the water present in the stream h1 being evaporated and solids present in the stream h1 being converted to a powder or granules. In a specific variant, the thermal treatment is conducted in a fluidized bed granulator.

In the last variant described, the stream h1 is subjected to a thermal treatment, with evaporation of the liquid present in the wastewater to obtain the organic substances present in the wastewater as solids in the form of powder and/or granules. This allows the remaining solids content to be removed without any great technical complexity. The solids content, which is small in terms of volume, can finally be drawn off as powder or granules and deposited in landfill or sent to an economically viable utilization.

Preferably, stream h1, prior to the thermal treatment, is not subjected to any further process step such as flocculation, filtration or centrifugation, as a result of which costly plant components, for example centrifuges, are dispensed with. However, it may be advantageous to reduce the content of volatile hydrocarbons in the wastewater by stripping. The solids present in the stream h1 may be present in dissolved and/or suspended form.

In a preferred variant, the thermal treatment is conducted in one or more fluidized bed granulators, in which case the stream h1 is sprayed onto a fluidization plate. Hot process air flowing through the tray from beneath evaporates the liquid present in the stream h1 and produces a fluidized bed from the solids through fluidization. In addition, the process air brings about the transport of the solids out of the granulator. The process air leaves the system in a mixture with the evaporated liquid via a suitable purifying apparatus, such as a filter, cyclone or scrubber.

In addition, the thermal treatment can also be conducted in other systems for drying of aqueous solutions of solids and/or suspensions of solids, for example in a screw drier.

According to the invention, in the cooling stage Ca), a biphasic dispersion of one or more organic solvents and an aqueous phase is used. The rapid cooling of the product gas stream in the quench results in condensation of high-boiling secondary components. Organic solvents generally have a very much higher dissolution capacity for the high-boiling by-products which can lead to deposits and blockages in the plant parts downstream of the ODH reactor than water or aqueous alkaline solutions. Organic solvents used with preference are aromatic hydrocarbons, more preferably toluene, o-xylene, m-xylene, p-xylene, mesitylene, mono-, di- and triethylbenzene, mono-, di- and triisopropylbenzene and mixtures thereof. A solvent used with very particular preference is mesitylene.

On the industrial scale, organic solvents are often unobtainable as pure substances, or else a high purity leads to very high costs. The organic solvent normally has a purity of more than 90% by weight, preferably of more than 94% by weight and more preferably of more than 96% by weight.

For example, technical grade mesitylene often comprises 90% by weight of pure mesitylene, preferably 94% by weight of mesitylene and more preferably 96% by weight of mesitylene. Typical impurities include other isomers of trimethylbenzene, isomers of dimethylbenzene and monomethylbenzene, and isomers of mono-, di- and triethylbenzene, mono-, di- and triisopropylbenzene, but also smaller amounts of further aromatic, especially alkylaromatic, compounds. It is likewise possible for small amounts of aliphatic secondary components to be present.

The presence of an additional aqueous phase in the circulating cooling medium can result in effective avoidance of blockages in the quench circuit, especially in the region of the nozzles through which the coolant enters the quench column, but also, for example, in the pumps of the coolant circuit and in analytical instruments which measure the volume flow rate of the circulation. This is attributed to the fact that the condensed high-boiling secondary components also include substances which have only a low solubility in an organic solvent but have significantly better solubility in water or aqueous solutions. The effect of this is that tackifying substances are dissolved in the organic and aqueous phase, the result of which is that coke-like insoluble solids remain dispersed in the coolant circuit, and are not deposited on plant parts such as nozzles and do not lead to blockages therein.

Preferably, the cooling medium on entry into the cooling zone has very good dispersion of the two phases. A basic measure used for the dispersion quality is a relative standard deviation $\sigma/\sigma 0$. See, for example, Kraume et al., "Continuous Mixing of Fluids" in Ullmann's Encyclopedia of Industrial Chemistry, Wiley-VCH (2012); or Streiff, Chem. Ing. Tech. 52, 520 (1980). The test method used is the conductivity test method according to Phal and Muschelknautz, Chem. Ing. Tech. 51, 347 (1979). In this method, the different electrical conductivities of aqueous and organic phase are exploited, and the electrical conductivity and hence the concentration of the two phases are measured with spatial resolution. An ideal dispersion would thus exist at $\sigma/\sigma 0=0$. Preferably, the components forming the organic phase and the components forming the aqueous phase in the biphasic cooling medium have a coefficient of variation of less than 1, preferably of less than 0.5, more preferably of less than 0.1.

A high degree of dispersion of the cooling medium can be effected, for example, through the incorporation of suitable mixers into the circuit. The type of mixer is not restricted any further here, and comprises stirrers, static mixers and restrictors.

In addition, a high degree of dispersion of the cooling medium can be achieved by means of a nozzle. For the Reynolds number Re of a flow generated in a nozzle, the following expression is adopted for each of the two phases of the coolant:

$$Re=(\rho \times v \times d)\eta$$

with $\rho$=density of the respective phase
$v$=flow rate of the respective phase
$d$=length (nozzle opening here)
$\eta$=dynamic viscosity of the respective phase For water having a circulation flow rate of 60 l/h, a nozzle opening of 1.15 mm and a dynamic viscosity of water at 20° C. of $10^{-3}$ Pa s, this gives, for example:

$$v=\text{volume flow rate/area}=1.66 \cdot 10^{-5}/(pi*(1.15/2 \cdot 10^{-3})^2)=16 \text{ m/s}$$

$Re = (1000 \text{ kg/m}^3 \times 16 \text{ m/s} \times 1.15 \ 10^{-3} \text{ m})/10^{-3} \text{ Pa s} = 18\,400.$ In general, the Reynolds number Re of the two phases of the cooling medium on entry into the cooling stage is greater than 100, preferably greater than 500 and more preferably greater than 1000.

A further crucial factor for a high degree of dispersion's a high volume-specific power input into the cooling medium. This can in turn be achieved, for example, by means of suitable mixers, pumps or nozzles.

The volume-specific power input $P_v$ is assumed to be:

$$P_V = \Delta p \dot{V}/(V)$$

with $\Delta p$=pressure drop over the power-introducing process unit
$\dot{V}$=circulation volume flow rate of the coolant
V=specific volume of the process unit For a cooling medium having a circulation volume flow rate of 60 l/h, a pressure drop over the nozzle of 500 mbar and a nozzle volume of 0.1 cm³, for example, this gives:

$$P_v = 500 \text{ mbar} \times 60 \text{ l/h}/10 \text{ mm}^3 = 5\cdot 10^4 \text{ (kg/ms}^2)\times 1.6\cdot 10^{-5} \text{ (m}^3\text{/s)}/10^{-7} \text{ m}^3 = 8\cdot 10^7 \text{ W/m}^3.$$

In general, the volume-specific power input into the coolant in circulation is at least $10^3$ W/m³, preferably at least $10^4$ W/m³, and more preferably at least $10^5$ W/m³.

In general, the cooling medium is fed into the cooling zone(s) through one or more nozzles. In a preferred embodiment, a flow with a Reynolds number Re of at least 1000 is produced here in the nozzle(s). The power input here is at least $10^3$ W/m³. More particularly, this achieves such good dispersion of the two phases that the coefficient of variation for each component of each phase of the cooling medium on entry into the cooling zones is less than 1.

Embodiments which follow are preferred or particularly preferred variants of the process according to the invention:

Stage Ca) is performed in multiple stages in stages Ca1) to Can), preferably in two stages Ca1) and Ca2). In this case, at least a portion of the cooling medium may be fed as coolant to the first stage Ca1) after it has passed through the second stage Ca2). If stage Ca) is conducted in multiple stages, a biphasic cooling medium is used at least in the first stage.

Stage Cb) generally comprises at least one compression stage Cba) and at least one cooling stage Cbb). Preferably, in the at least one cooling stage Cbb), the gas compressed in the compression stage Cba) is contacted with a coolant. More preferably, the coolant in the cooling stage Cbb) comprises the same organic solvent which is used as a coolant in stage Ca). In an especially preferred variant, at least some of this coolant is fed as a coolant to stage Ca) after it has passed through the at least one cooling stage Cbb). This coolant too may be a biphasic dispersion of an organic solvent and an aqueous phase.

Preferably, stage Cb) comprises a plurality of compression stages Cba1) to Cban) and cooling stages Cbb1) to Cbbn), for example four compression stages Cba1) to Cba4) and four cooling stages Cbb1) to Cbb4).

Preferably, step D) comprises steps Da) to Dc);

Da) absorbing the $C_4$ hydrocarbons comprising butadiene and n-butenes in a high-boiling absorbent, giving an absorbent stream laden with $C_4$ hydrocarbons and the gas stream d2, Db) removing oxygen from the absorbent stream laden with $C_4$ hydrocarbons from step Da) by stripping with an uncondensable gas stream, and Dc) desorbing the $C_4$ hydrocarbons from the laden absorbent stream, giving a $C_4$ product gas stream d1 consisting essentially of $C_4$ hydrocarbons and comprising less than 100 ppm of oxygen.

Preferably, the high-boiling absorbent used in step Da) is an aromatic hydrocarbon solvent, more preferably the aromatic hydrocarbon solvent used in step Ca), especially toluene, o-xylene, m-xylene, p-xylene, mesitylene or mixtures thereof. Mesitylene is especially preferred.

In a step A), an input gas stream comprising n-butenes is provided.

Input gas streams used may be pure n-butenes (1-butene and/or cis/trans-2-butene), but also gas mixtures comprising butenes. Such a gas mixture can be obtained, for example, by nonoxidative dehydrogenation of n-butane. It is also possible to use a fraction which comprises n-butenes (1-butene and cis/trans-2-butene) as the main constituent and has been obtained from the $C_4$ fraction from naphtha cracking by removal of butadiene and isobutene. In addition, it is also possible to use, as input gas, gas mixtures which comprise pure 1-butene, cis-2-butene, trans-2-butene or mixtures thereof, and which have been obtained by dimerization of ethylene. In addition, input gases used may be gas mixtures which comprise n-butenes and have been obtained by catalytic fluidized bed cracking (fluid catalytic cracking, FCC).

In one embodiment of the process according to the invention, the input gas comprising n-butenes is obtained by nonoxidative dehydrogenation of n-butane. Through the coupling of a nonoxidative catalytic dehydrogenation with the oxidative dehydrogenation of the n-butenes formed, it is possible to obtain a high yield of butadiene, based on n-butane used. The nonoxidative catalytic n-butane dehydrogenation gives a gas mixture which, as well as butadiene, 1-butene, 2-butenes and unconverted n-butane, comprises secondary constituents. Typical secondary constituents are hydrogen, water vapor, nitrogen, CO and $CO_2$, methane, ethane, ethene, propane and propene. The composition of the gas mixture leaving the first dehydrogenation zone may vary significantly depending on the mode of operation of the dehydrogenation. For instance, in the case of performance of the dehydrogenation while feeding in oxygen and additional hydrogen, the product gas mixture has a comparatively high content of water vapor and carbon oxides. In the case of modes of operation without feeding of oxygen, the product gas mixture of the nonoxidative dehydrogenation has a comparatively high content of hydrogen.

In step B), the input gas stream comprising n-butenes and at least one oxygenous gas are fed into at least one dehydrogenation zone and the butenes present in the gas mixture are oxidatively dehydrogenated to butadiene in the presence of an oxydehydrogenation catalyst.

Catalysts suitable for the oxydehydrogenation are generally based on an Mo—Bi—O-containing multimetal oxide system which generally additionally comprises iron. In general, the catalyst system also comprises further additional components, for example potassium, cesium, magnesium, zirconium, chromium, nickel, cobalt, cadmium, tin, lead, germanium, lanthanum, manganese, tungsten, phosphorus, cerium, aluminum or silicon. Iron-containing ferrites have also been proposed as catalysts.

In a preferred embodiment, the multimetal oxide comprises cobalt and/or nickel. In a further preferred embodiment, the multimetal oxide comprises chromium. In a further preferred embodiment, the multimetal oxide comprises manganese.

Examples of Mo—Bi—Fe—O-containing multimetal oxides are Mo—Bi—Fe—Cr—O— or Mo—Bi—Fe—Zr—O-containing multimetal oxides. Preferred systems are described, for example, in U.S. Pat. No. 4,547,615 ($Mo_{12}BiFe_{0.1}Ni_8ZrCr_3K_{0.2}O_x$ and $Mo_{12}BiFe_{0.1}Ni_8AlCr_3K_{0.2}O_x$), U.S. Pat. No. 4,424,141 ($Mo_{12}BiFe_3Co_{4.5}Ni_{2.5}P_{0.5}K_{0.1}O_x+SiO_2$), DE-A 25 30 959 ($Mo_{12}BiFe_3Co_{4.5}Ni_{2.5}Cr_{0.5}K_{0.1}O_x$, $Mo_{13.75}BiFe_3Co_{4.5}Ni_{2.5}Ge_{0.5}K_{0.8}O_x$, $Mo_{12}BiFe_3Co_{4.5}Ni_{2.5}Mn_{0.5}K_{0.1}O_x$ and $Mo_{12}BiFe_3Co_{4.5}Ni_{2.5}La_{0.5}K_{0.1}O_x$), U.S. Pat. No. 3,911,039 ($Mo_{12}BiFe_3Co_{4.5}Ni_{2.5}Sn_{0.5}K_{0.1}O_x$), DE-A 25 30 959 and DE-A 24 47 825 ($Mo_{12}BiFe_3Co_{4.5}Ni_{2.5}W_{0.5}K_{0.1}O_x$).

Suitable multimetal oxides and the preparation thereof are additionally described in U.S. Pat. No. 4,423,281 ($Mo_{12}BiNi_8Pb_{0.5}Cr_3K_{0.2}O_x$ and $Mo_{12}Bi_bNi_7Al_3Cr_{0.5}K_{0.5}O_x$), U.S. Pat. No. 4,336,409 ($Mo_{12}BiNi_6Cd_2Cr_3P_{0.5}O_x$), DE-A 26 00 128 ($Mo_{12}BiNi_{0.5}Cr_3P_{0.5}Mg_{7.5}K_{0.1}O_x+SiO_2$) and DE-A 24 40 329 ($Mo_{12}BiCo_{4.5}Ni_{2.5}Cr_3P_{0.5}K_{0.1}O_x$).

Particularly preferred catalytically active multimetal oxides comprising molybdenum and at least one further metal have the general formula (Ia):

$$Mo_{12}Bi_aFe_bCo_cNi_dCr_eX^1_fX^2_gO_y \qquad (Ia)$$

with
X$^1$=Si, Mn and/or Al,
X$^2$=Li, Na, K, Cs and/or Rb,
0.2≤a≤1,
0.5≤b≤10,
0≤c≤10,
0≤d≤10,
2≤c+d≤10
0≤e≤2,
0≤f≤10,
0≤g≤0.5,
y=a number which, with the prerequisite of charge neutrality, is determined by the valency and frequency of the elements in (Ia) other than oxygen.

Preference is given to catalysts whose catalytically active oxide composition, of the two metals Co and Ni, has only Co (d=0). Preferred is X$^1$ Si and/or Mn and X$^2$ is preferably K, Na and/or Cs, more preferably X$^2$=K.

The molecular oxygen-comprising gas comprises generally more than 10% by volume, preferably more than 15% by volume and even more preferably more than 20% by volume of molecular oxygen. It is preferably air. The upper limit for the content of molecular oxygen is generally 50% by volume or less, preferably 30% by volume or less and even more preferably 25% by volume or less. In addition, any desired inert gases may be present in the molecular oxygen-comprising gas. Possible inert gases may include nitrogen, argon, neon, helium, CO, CO$_2$ and water. The amount of inert gases, for nitrogen, is generally 90% by volume or less, preferably 85% by volume or less and even more preferably 80% by volume or less. In the case of constituents other than nitrogen, it is generally 10% by volume or less, preferably 1% by volume or less.

For performance of the oxidative dehydrogenation at full conversion of n-butenes, preference is given to a gas mixture having a molar oxygen:n-butenes ratio of at least 0.5. Preference is given to working at an oxygen:n-butenes ratio of 0.55 to 10. To set this value, the input gas can be mixed with oxygen or one or more oxygenous gases, for example air, and optionally additional inert gas or water vapor. The oxygenous gas mixture obtained is then fed to the oxydehydrogenation.

The reaction temperature in the oxydehydrogenation is generally controlled by a heat exchange medium present around the reaction tubes. Examples of useful liquid heat exchange media of this kind include melts of salts such as potassium nitrate, potassium nitrite, sodium nitrite and/or sodium nitrate, and melts of metals such as sodium, mercury and alloys of various metals. It is also possible to use ionic liquids or heat carrier oils. The temperature of the heat exchange medium is between 220 and 490° C., preferably between 300 and 450° C. and more preferably between 350 and 420° C.

Because of the exothermicity of the reactions which proceed, the temperature in particular sections of the reaction interior during the reaction may be higher than that of the heat exchange medium, and what is called a hotspot develops. The position and magnitude of the hotspot is decided by the reaction conditions, but it can also be regulated through the dilution ratio of the catalyst layer or the flow rate of mixed gas. The difference between hotspot temperature and the temperature of the heat exchange medium is generally between 1-150° C., preferably between 10-100° C. and more preferably between 20-80° C. The temperature at the end of the catalyst bed is generally between 0-100° C., preferably between 0.1-50° C., more preferably between 1-25° C., above the temperature of the heat exchange medium.

The oxydehydrogenation can be performed in all fixed bed reactors known from the prior art, for example in a staged oven, in a fixed bed tubular reactor or shell and tube reactor, or in a plate heat exchanger reactor. A shell and tube reactor is preferred.

Preferably, the oxidative dehydrogenation is performed in fixed bed tubular reactors or fixed bed shell and tube reactors. The reaction tubes (just like the other elements of the shell and tube reactor) are generally manufactured from steel. The wall thickness of the reaction tubes is typically 1 to 3 mm. The internal diameter thereof is generally (uniformly) 10 to 50 mm or 15 to 40 mm, frequently 20 to 30 mm. The number of reaction tubes accommodated in a shell and tube reactor generally runs to at least 1000, or 3000, or 5000, preferably to at least 10 000. Frequently, the number of reaction tubes accommodated in a shell and tube reactor is 15 000 to 30 000, or to 40 000 or to 50 000. The length of the reaction tubes normally extends to a few meters, a typical reaction tube length being in the range from 1 to 8 m, frequently 2 to 7 m, in many cases 2.5 to 6 m.

The invention is elucidated in detail hereinafter with reference to FIGS. 1 to 4.

The catalyst bed installed in the ODH reactor 1 may consist of a single layer or of 2 or a sequence of variable layers (called a structured bed). These layers may consist of a pure catalyst or be diluted with a material which does not react with the input gas or components from the product gas of the reaction. In addition, the catalyst layers may consist of shaped bodies of unsupported material or supported eggshell catalysts.

The product gas stream 2 leaving the oxidative dehydrogenation comprises, as well as butadiene, generally also unconverted 1-butene and 2-butene, oxygen and water vapor. As secondary components, it generally further comprises carbon monoxide, carbon dioxide, inert gases (principally nitrogen), low-boiling hydrocarbons such as methane, ethane, ethene, propane and propene, butane and isobutane, with or without hydrogen and with or without oxygen-containing hydrocarbons, called oxygenates. Oxygenates may, for example, be formaldehyde, furan, acetaldehyde, acetic acid, maleic anhydride, formic acid, methacrolein, methacrylic acid, crotonaldehyde, crotonic acid, propionaldehyde, propionic acid, acrolein, acrylic acid, methyl vinyl ketone, styrene, benzaldehyde, benzoic acid, phthalic anhydride, fluorenone, anthraquinone and butyraldehyde.

The product gas stream 2 at the reactor outlet is characterized by a temperature close to the temperature at the end of the catalyst bed. The product gas stream is then brought to a temperature of 150-400° C., preferably 160-300° C., more preferably 170-250° C. It is possible to insulate the line through which the product gas stream flows, or to use a heat exchanger, in order to keep the temperature within the desired range. Any heat exchanger system is possible, provided that this system can be used to keep the temperature of the product gas at the desired level. Examples of a heat exchanger include spiral heat exchangers, plate heat exchangers, double tube heat exchangers, multitube heat exchangers, boiler-spiral heat exchangers, boiler-shell heat exchangers, liquid-liquid contact heat exchangers, air heat exchangers, direct contact heat exchangers and fin tube heat exchangers. Since, while the temperature of the product gas is set to the desired temperature, some of the high-boiling by-products present in the product gas can precipitate out, the heat exchanger system should therefore preferably have two or more heat exchangers. If two or more heat exchangers provided are arranged in parallel in this case, and distributed cooling of the product gas obtained in the heat exchangers is thus enabled, the amount of high-boiling by-products which are deposited in the heat exchangers decreases, and hence the service life thereof can be extended. As an alternative to the abovementioned method, the two or more heat exchangers provided may be arranged in parallel. The product gas is supplied to one or more, but not to all, heat exchangers, which are succeeded by other heat exchangers after a certain operation period. In the case of this method, the cooling can be continued, some of the heat of reaction can be recovered and, in parallel, the high-boiling by-products deposited in one of the heat exchangers can be removed. It is possible to use a solvent as an abovementioned organic solvent, provided that it is capable of dissolving the high-boiling by-products. Examples are aromatic hydrocarbon solvents, for example toluene and xylenes and mesitylene, and alkaline aqueous solvents, for example the aqueous solution of sodium hydroxide.

Subsequently, a majority of the high-boiling secondary components and of the water is removed from the product gas stream 2 by cooling and compression. According to the invention, the cooling is effected by contacting with a biphasic cooling medium comprising an aqueous phase and an organic phase. This stage is also referred to hereinafter as the quench. This quench may consist of only one stage (3 in FIGS. 1-3) or of a plurality of stages (for example 3, 8 in FIGS. 1-3). Product gas stream 2 is thus contacted directly with a biphasic cooling medium 6 and hence cooled. The organic phase comprises organic solvents, preferably aromatic hydrocarbons, more preferably toluene, o-xylene, m-xylene, p-xylene, mesitylene, all the possible constitutional isomers of mono-, di- and triethylbenzene, or mixtures thereof. Preference is also given to aromatic hydrocarbons having a boiling point at 1013.25 hPa of more than 120° C., or mixtures thereof.

In general, product gas 2, according to the presence and temperature level of any heat exchanger upstream of the quench 3, has a temperature of 100-440° C. The product gas is contacted in the quench stage 3 with the cooling medium composed of aqueous and organic phase. In this operation, the cooling medium is introduced preferably through a nozzle, in order to achieve very efficient mixing of the aqueous and organic phases on the one hand, and of the biphasic cooling medium with the product gas on the other hand. For the same purpose, it is possible to introduce internals, for example further nozzles, in the quench stage, through which the product gas and the cooling medium pass together. The coolant inlet into the quench is designed such that blockage by deposits in the region of the coolant inlet is minimized.

In general, product gas 2 is cooled in the first quench stage 3 to 5 to 180° C., preferably to 30 to 130° C. and even more preferably to 50 to 110° C. The temperature of the cooling medium 6 at the inlet may generally be 5 to 200° C., preferably 20 to 120° C., especially preferably 30 to 90° C. The pressure in the first quench stage 3 is not particularly restricted, but is generally 0.01-5 bar (g), preferably 0.1-2 bar (g) and more preferably 0.2-3 bar (g). If any great amounts of high-boiling by-products are present in the product gas, high-boiling by-products may readily polymerize and result in deposits of solids which are caused by high-boiling by-products in this process section. In general, the quench stage 3 is configured as a cooling tower. The cooling medium 6 used in the cooling tower is used in circulating form in a quench circuit. The circulation can be ensured by means of a suitable pump. The temperature of the cooling medium in the quench circuit can optionally be controlled by a heat exchanger. The circulation flow rate of the cooling medium in liters per hour, based on the mass flow rate of butadiene in grams per hour, may generally be 0.0001-5 l/g, preferably 0.001-1 l/g and more preferably 0.002-0.2 l/g.

The temperature of the biphasic cooling medium 6 in the pot may generally be 15-210° C., preferably 25-130° C., especially preferably 35-95° C. According to the temperature, pressure and water content of product gas 2, there may additionally be condensation of water in the first quench stage 3. Since the loading of the organic phase and the aqueous phase with secondary components increases over the course of time, a portion of the cooling medium is drawn off from the circulation as purge stream 6b and the circulation rate can be kept constant by addition of organic phase 5a with lower loading and of aqueous phase 4a with lower loading. The ratio of output volume and addition volume depends on the steam loading of the product gas and the product gas temperature at the end of the first quench stage. The locations for the feeds and withdrawals are not subject to any further restriction. They may, for example, be upstream of or beyond the pump or the heat exchanger. The purge stream 6b is subsequently separated into an aqueous phase and an organic phase, the aqueous phase being worked up further in accordance with the invention as aqueous purge stream g.

Figure 2:
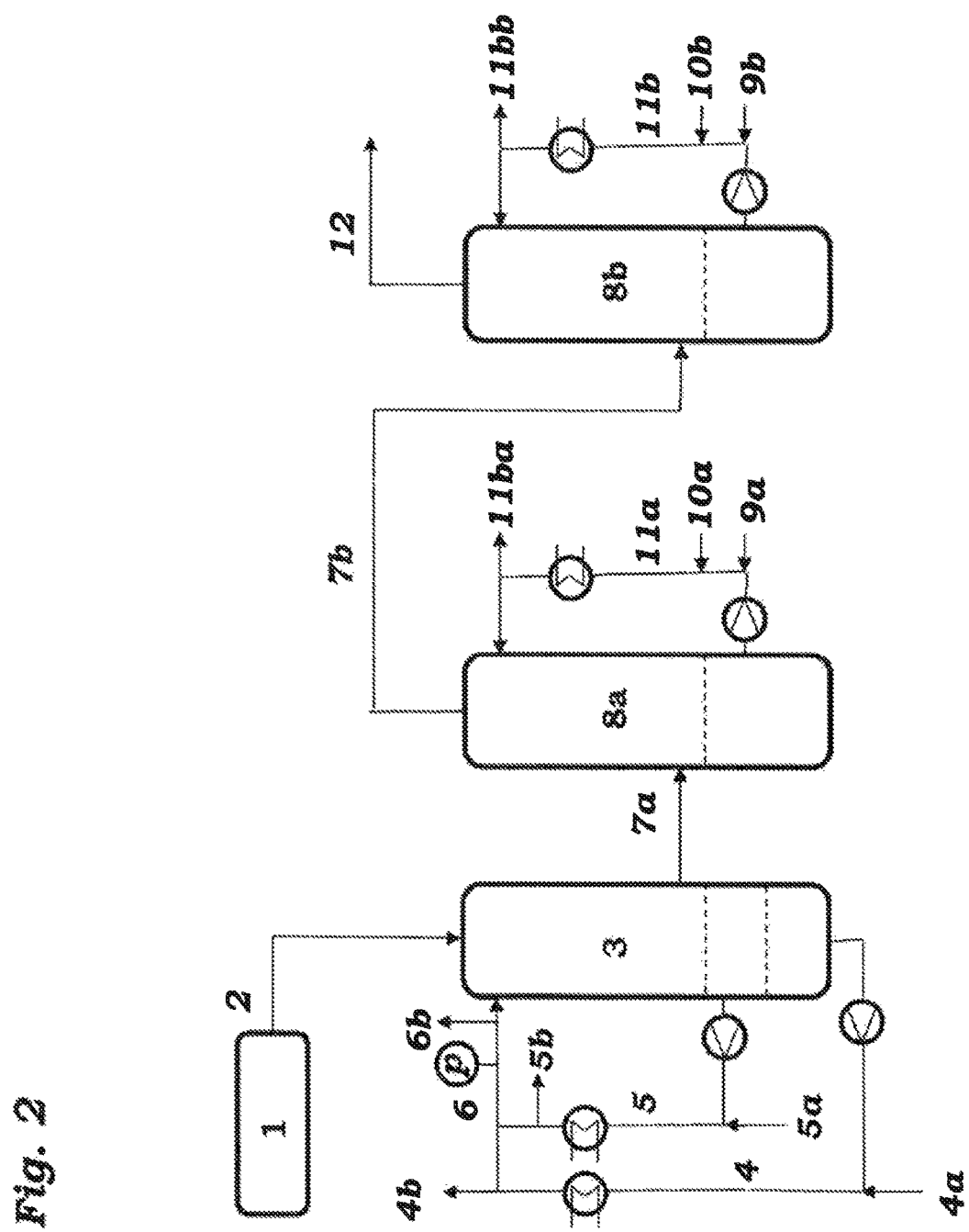
FIG. 2 is a schematic diagram of the reaction process with second and third quench stage.
Figure 3:
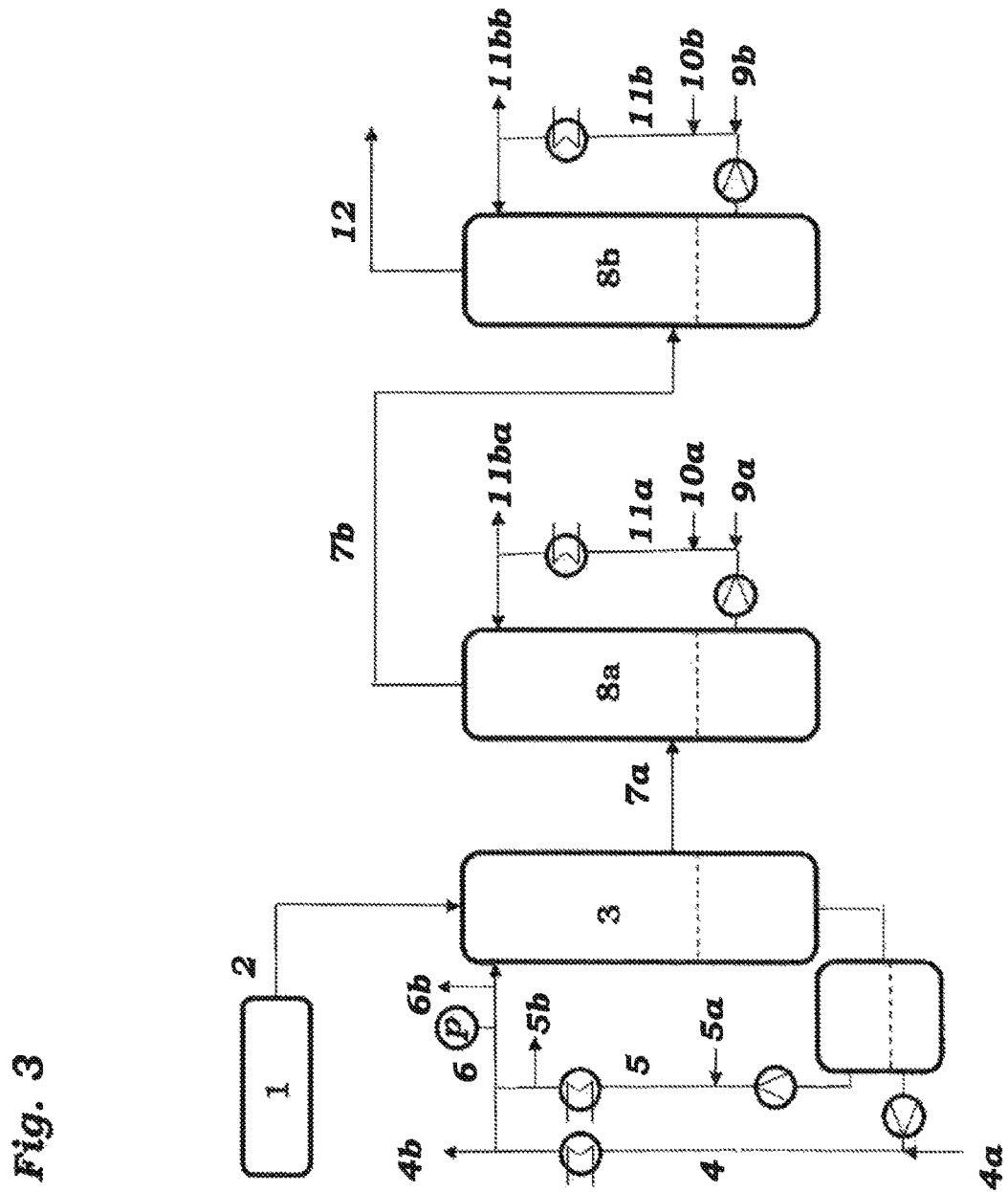
FIG. 3 is a schematic diagram of the reaction process with second and third quench stage.

In the bottom of the quench stage 3, a predominantly aqueous phase 4 may form, which additionally comprises water-soluble secondary components. This can, as shown in FIG. 2, be drawn off from the bottom of the quench stage 3 and recycled. The aqueous phase 4 may also, as shown in FIG. 3, be removed in an additional phase separator. This may, for example, be within the quench circuit. The aqueous phase 4 is at least partly recycled into the quench. The organic phase 5 too is at least partly recycled into the quench. Instead of or in addition to the purge stream 6b, it is also possible to remove an aqueous purge stream 4b and an organic purge stream 5b.

The aqueous purge stream 4b, optionally together with the aqueous stream resulting from the purge stream 6b, is worked up further in accordance with the invention as aqueous purge stream g.

In a preferred embodiment, the quench has two stages (comprising stages 3 and 8a according to FIGS. 1-3), i.e. stage Ca) comprises two cooling stages Ca1) and Ca2) in which the product gas stream b is contacted with the cooling medium. According to the invention, at least the cooling medium in the first cooling stage Ca1) is biphasic. The quench stages Ca1) and Ca2) may be in separate cooling towers or in a common cooling tower.

In this case, the cooled product gas stream 7a, which may have been depleted of secondary components, is sent to a second quench stage 8a. In this stage, it is contacted again with a cooling medium 11a. The cooling medium 11a may be biphasic and may comprise an aqueous phase and an organic phase. However, it may also consist predominantly or exclusively of an organic solvent.

Preferably, the organic solvent comprises aromatic hydrocarbons, more preferably toluene, o-xylene, m-xylene, p-xylene, mesitylene, all the possible constitutional isomers of mono-, di- and triethylbenzene and all the possible constitutional isomers of mono-, di- and triisopropylbenzene, or mixtures thereof. Preference is also given to aromatic hydrocarbons having a boiling point at 1013.25 hPa of more than 120° C., or mixtures thereof. The organic solvent is preferably the same as in the first quench stage.

In general, the product gas, up to the gas outlet of the second quench stage 8a, is cooled to 5 to 100° C., preferably to 15-85° C. and more preferably to 20-70° C. The coolant can be fed in countercurrent to the product gas. In this case, the temperature of the coolant medium 11a at the coolant inlet may be 5-100° C., preferably 15-85° C., especially preferably 30-70° C. The pressure in the second quench stage 8a is not particularly restricted, but is generally 0.01-4 bar (g), preferably 0.1-2 bar (g) and more preferably 0.2-1 bar (g). The second quench stage 8a is preferably configured as a cooling tower. The cooling medium 11a used in the cooling tower is used in circulating form in a quench circuit. The circulation flow rate of the cooling medium 11a in liters per hour, based on the mass flow rate of butadiene in grams per hour, may generally be 0.0001-5 l/g, preferably 0.001-1 l/g and more preferably 0.002-0.2 l/g.

Since the loading of the cooling medium 11a with secondary components increases over the course of time, a portion of the cooling medium can be drawn off from the circulation as purge stream 11ba and the circulation rate can be kept constant by addition of organic phase 10a with lower loading and optionally of aqueous phase 9a with lower loading.

The temperature of the cooling medium 11a in the pot may generally be 20-210° C., preferably 35-120° C., especially preferably 45-85° C. According to the temperature, pressure and water content of product gas 7a, there may additionally be condensation of water in the second quench stage 8a. In this case, an additional aqueous phase may form in the column bottom. The aqueous phase may also be removed in an additional phase separator. This may, for example, be within the quench circuit. The aqueous phase can be drawn off or at least partly recycled into the quench. Alternatively, the phase separator may be present, for example, in the purge stream 11ba.

The aqueous phase may at least partly be drawn off as a purge stream or at least partly be recycled into the quench. The organic phase may likewise at least partly be drawn off as a purge stream or at least partly be recycled into the quench.

The locations for the feeds and withdrawals in the circuits of the respective quench stages are not subject to any further restriction. They may, for example, be upstream of or beyond the pump or the heat exchanger. In addition, the location of the heat exchanger(s) in the quench circuit is not subject to any further restriction. In the case of partly phase-separated quench circuits, heat exchangers may be present in one or both circuits, or only in the recombined circuits. Alternatively, it is possible to entirely dispense with a heat exchanger, and the quench cooling may be accomplished solely through evaporation of the coolant. In addition, the location of the circulation pumps is not subject to any further restriction. In the case of a phase separator in the circulation stream, for example, a pump may be present upstream of the phase separator, or one pump may be present in each of the phase-separated circuits.

In order to achieve very good contact of product gas and cooling medium, internals may be present in the second quench stage 8. Internals of this kind include, for example, bubble-cap, centrifugal and/or sieve trays, columns having structured packings, for example sheet metal packings having a specific surface area of 100 to 1000 $m^2/m^3$, such as Mellapak® 250 Y, and columns having random packings.

The coolant circulation streams of the quench stages may either be separate from one another or combined with one another. For example, a portion of stream 11ba may be supplied to stream 6 and at least partly replace streams 4a and/or 5a. The desired temperature of the circulation streams can be set by means of suitable heat exchangers.

In a preferred embodiment of the invention, the cooling stage Ca) is thus performed in two stages, in which case the organic solvent laden with secondary components from the second stage Ca2) is conducted into the first stage Ca1). The organic solvent withdrawn from the second stage Ca2) comprises a lower level of secondary components than the organic solvent withdrawn from the first stage Ca1).

Stage Ca) can also be performed in multiple stages in stages Ca1) to Can), more preferably in three stages Ca1), Ca2) and Ca3). In this case, at least a portion of the cooling medium may be fed as coolant to the second stage Ca2) after it has passed through the third stage Ca3).

In a particularly preferred embodiment, the quench has three stages (comprising stages 3, 8a and 8b according to FIGS. 1-3), i.e. stage Ca) comprises three cooling stages Ca1), Ca2) and Ca3) in which the product gas stream b is contacted with the cooling medium. According to the invention, at least the cooling medium in the first quench stage Ca1) is biphasic. The three cooling stages may be in separate cooling towers or in a common cooling tower.

In this case, the cooled product gas stream 7a, which may have been depleted of secondary components, is sent to a second quench stage 8a and to a third quench stage 8b. In these quench stages, it is contacted again with a cooling medium 11b. The cooling medium may be biphasic and may comprise an aqueous phase and an organic phase. However, it may also consist predominantly or exclusively of an organic solvent.

Preferably, the organic solvent in all three quench stages is the same.

The coolant circulation streams of the three quench stages may either be separate from one another or combined with one another.

In a particularly preferred embodiment of the invention, the cooling stage Ca) is thus conducted in three stages, in which case the organic solvent laden with secondary components from the second stage Ca2) is conducted into the first stage Ca1), and the organic solvent less heavily laden with secondary components from the third stage Ca3) is conducted into the second stage Ca2).

In a further embodiment, in the third cooling stage Ca3), a fresh cooling medium composed of an organic solvent or a mixture of organic solvent and water, said cooling medium being as yet unladen with the secondary components, is fed into the cooling stage in single pass and in countercurrent. Since the fresh cooling medium is as yet unladen with the secondary components to be removed in the quench stages, a further reduction in the secondary components unwanted in the product gas is achieved in the top product of the cooling tower.

In order to assure the liquid space velocity required for the design of the cooling tower in the cooling stage Ca3), the diameter chosen for this cooling stage Ca3) may be smaller than the diameter of the cooling stages Ca1) and Ca2). If the required liquid space velocity in the cooling stage Ca3) cannot be achieved by reducing the diameter, the liquid space velocity in this section is increased correspondingly by pumped circulation of the cooling medium.

In one embodiment of the invention, the first cooling stage Ca1) has a parallel and interchangeable configuration. In normal operation, only one of the two parallel cooling stages is operated, while the other is kept out of operation for cleaning operations or is available as a reserve.

In order to minimize the entrainment of liquid constituents from the quench into the offgas line, suitable construction measures, for example the installation of a demister, can be taken. In addition, high-boiling and other substances which are not separated from the product gas in the quench can be removed from the product gas through further construction measures, for example further gas scrubbing operations.

A gas stream 12 is obtained, which comprises n-butane, 1-butene, 2-butenes and butadiene, with or without oxygen, hydrogen and water vapor, and small amounts of methane, ethane, ethene, propane and propene, isobutane, carbon oxides, inert gases and portions of the solvent used in the quench. In addition, traces of high-boiling components which have not been removed quantitatively in the quench may remain in this gas stream 12.

Subsequently, the gas stream b from the cooling step Ca), which has been depleted of high-boiling secondary components, is cooled in step Cb) in at least one compression stage Cba) and preferably in at least one cooling stage Cbb) by contacting with an organic solvent as a coolant.

Figure 4:
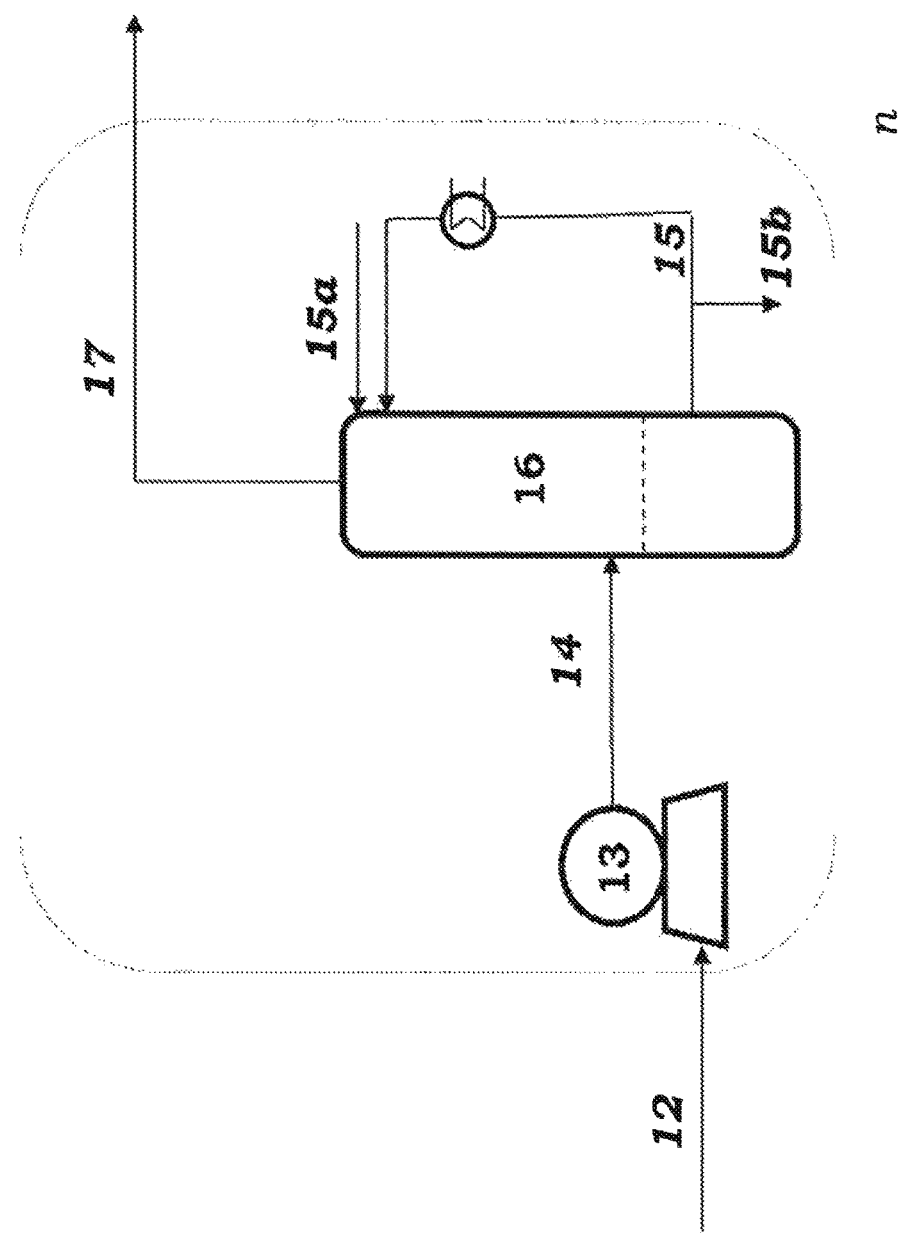
FIG. 4 is a schematic diagram of the reaction process with a compression stage and cooling a cooling stage.

Product gas stream 12 from the coolant quench (3, or preferably 3 and 8a, or preferably 3, 8a and 8b) is, as shown in FIG. 4, compressed in at least one compression stage 13 and subsequently cooled further in the cooling apparatus 16.

The compression and cooling of the gas stream 12 can be effected in one or more stages (n stages). In general, compression is effected overall from a pressure in the range from 1.0 to 4.0 bar (absolute) to a pressure in the range from 3.5 to 20 bar (absolute). Each compression stage is followed by a cooling stage in which the gas stream is cooled to a temperature in the range from 15 to 60° C. The cooling can be effected by direct or indirect heat exchange.

In order to directly cool stream 14 and/or to remove further secondary components from stream 14, stream 14 is contacted with a coolant 15. The cooling medium 15 may be monophasic or biphasic and may comprise an aqueous phase and an organic phase. The organic phase comprises, in a preferred execution, the same organic solvent as the quench coolants 6, 11a and 11b. As a result of the cooling, there is condensation of water and of organic solvent used in the quench and possibly of further secondary components. Since the loading of the coolant 15 with secondary components increases over the course of time, a portion of the laden coolant can be drawn off as stream 15b from the circuit, and the circulation rate of the coolant can be kept constant by adding coolant 15a with lower loading.

The coolant 15 can be cooled in a heat exchanger and recycled as coolant into the apparatus 16.

The condensate stream 15b can be fed into stream 5a and/or 10a and/or 10b, and hence recycled into the circulation stream 6 and/or 11a and/or 11b of the quench. As a result, the $C_4$ components absorbed in the condensate stream 15a can be brought back into the gas stream, and hence the yield can be increased.

What remains is a gas stream 17 comprising butadiene, 1-butene, 2-butenes, oxygen and water vapor, with or without low-boiling hydrocarbons such as methane, ethane, ethene, propane and propene, butane and isobutane, with or without carbon oxides and with or without inert gases. In addition, this product gas stream may also comprise traces of high-boiling components.

Suitable compressors are, for example, turbo compressors, rotary piston compressors and reciprocating piston compressors. The compressors may be driven, for example, with an electric motor, an expander or a gas or steam turbine. Typical compression ratios (outlet pressure: inlet pressure) per compressor stage are between 1.5 and 3.0 according to the design. The compressed gas is cooled with organic solvent-purged heat exchangers or organic quench stages, which may take the form, for example, of shell and tube, spiral or plate heat exchangers. The coolants used in the heat exchangers are cooling water or heat carrier oils. In addition, preference is given to using air cooling with use of blowers.

The gas stream 17 comprising butadiene, n-butenes, oxygen, low-boiling hydrocarbons (methane, ethane, ethene, propane, propene, n-butane, isobutane), with or without water vapor, with or without carbon oxides and with or without inert gases and with or without traces of secondary components is fed as an output stream to further processing.

Figure 5:
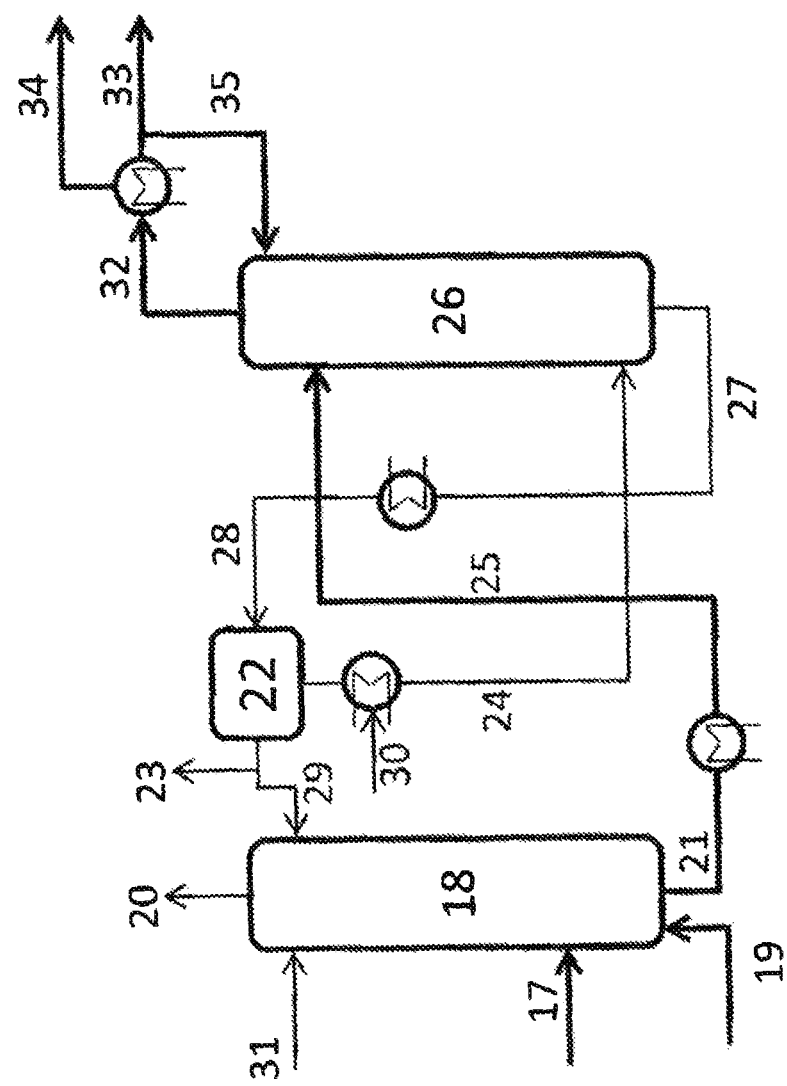
FIG. 5 is a schematic diagram of the reaction process with a separation phase of gases and low boiling hydrocarbons.

In a step D) shown in FIG. 5, uncondensable and low-boiling gas constituents comprising oxygen, low-boiling hydrocarbons (methane, ethane, ethene, propane, propene), carbon oxides and inert gases are separated in an absorption column as gas stream from the process gas stream 17 by absorption of the $C_4$ hydrocarbons in a high-boiling absorbent (29 and/or 31) and subsequent desorption of the 04 hydrocarbons. Preferably, step D), as shown in FIG. 5, comprises steps Da) to Dc):

Da) absorbing the 04 hydrocarbons comprising butadiene and n-butenes in a high-boiling absorbent (29 and/or 31), giving an absorbent stream laden with $C_4$ hydrocarbons and the gas stream 20, Db) removing oxygen from the absorbent stream laden with $C_4$ hydrocarbons from step Da) by stripping with an uncondensable gas stream 19, giving an absorbent stream 21 laden with $C_4$ hydrocarbons, and Dc) desorbing the $C_4$ hydrocarbons from the laden absorbent stream, giving a $C_4$ product gas stream 32 consisting essentially of $C_4$ hydrocarbons.

For this purpose, in the absorption stage 18, gas stream 17 is contacted with an inert absorbent and the $C_4$ hydrocarbons are absorbed in the inert absorbent, giving an absorbent laden with $C_4$ hydrocarbons and an offgas 20 comprising the other gas constituents. In a desorption stage, the $C_4$ hydrocarbons are released again from the high-boiling absorbent.

The absorption stage can be conducted in any desired suitable absorption column known to those skilled in the art. The absorption can be effected by simply passing the product gas stream through the absorbent. However, it can also be effected in columns or in rotary absorbers. It is possible to work in cocurrent, countercurrent or crosscurrent. The absorption is preferably conducted in countercurrent. Suitable absorption columns are, for example, tray columns having bubble-cap, centrifugal and/or sieve trays, columns having structured packings, for example sheet metal packings having a specific surface area of 100 to 1000 m$^2$/m$^3$, such as Mellapak® 250 Y, and columns having random packings. Also useful, however, are trickle towers and spray towers, graphite block absorbers, surface absorbers such as thick-layer and thin-layer absorbers, and also rotary columns, pan scrubbers, cross-spray scrubbers and rotary scrubbers.

In one embodiment, the gas stream 17 comprising butadiene, n-butenes and the low-boiling and uncondensable gas constituents is supplied to an absorption column in the lower region. In the upper region of the absorption column, the high-boiling absorbent (29 and/or 31) is introduced. Inert absorption media used in the absorption stage are generally high-boiling nonpolar solvents in which the C$_4$ hydrocarbon mixture to be separated off has a significantly higher solubility than the remaining gas components to be separated off. Suitable absorbents are comparatively nonpolar organic solvents, for example aliphatic C$_8$- to C$_{18}$-alkanes, or aromatic hydrocarbons such as the middle oil fractions from paraffin distillation, toluene or ethers having bulky groups, or mixtures of these solvents, to which a polar solvent such as dimethyl 1,2-phthalate may be added. Suitable absorbents are additionally esters of benzoic acid and phthalic acid with straight-chain C$_1$-C$_8$-alkanols, and what are called heat carrier oils, such as biphenyl and diphenyl ethers, chorine derivatives thereof and triarylalkenes. A suitable absorbent is a mixture of biphenyl and diphenyl ether, preferably in the azeotropic composition, for example the commercially available Diphyl®. Frequently, this solvent mixture comprises dimethyl phthalate in an amount of 0.1% to 25% by weight.

In a preferred embodiment, the same solvent is used in the absorption stage Da) as in the cooling stage Ca).

Preferred absorbents are solvents having a dissolution capacity for organic peroxides of at least 1000 ppm (mg of active oxygen/kg of solvent). In the preferred embodiment, the solvent used for the absorption is toluene, o-xylene, m-xylene, p-xylene, mesitylene or mixtures thereof.

At the top of the absorption column 18, an offgas stream 20 is drawn off, comprising essentially oxygen and low-boiling hydrocarbons (methane, ethane, ethene, propane, propene), with or without C$_4$ hydrocarbons (butane, butenes, butadiene), with or without inert gases, with or without carbon oxides and with or without water vapor. This stream can be supplied partly to the ODH reactor. It is thus possible, for example, to adjust the inlet stream of the ODH reactor to the desired C$_4$ hydrocarbon content.

At the bottom of the absorption column, in a further column, purging with a gas 19 discharges residues of oxygen dissolved in the absorbent. The remaining oxygen content should be sufficiently small that the stream 32 which comprises butane, butene and butadiene and leaves the desorption column comprises only a maximum of 100 ppm of oxygen.

The stripping of the oxygen in step Db) can be performed in any desired suitable column known to those skilled in the art. The stripping can be effected by simply passing uncondensable gases, preferably inert gases such as nitrogen, through the laden absorption solution. C$_4$ hydrocarbons additionally stripped out are washed back into the absorption solution in the upper portion of the absorption column 18, by passing the gas stream back into this absorption column. This can be effected either by means of pipe connection of the stripper column or direct mounting of the stripper column below the absorber column. This direct coupling can be effected since the pressure in the stripping column section and absorption column section is the same in accordance with the invention. Suitable stripping columns are, for example, tray columns having bubble-cap, centrifugal and/or sieve trays, columns having structured packings, for example sheet metal packings having a specific surface area of 100 to 1000 m$^2$/m$^3$, such as Mellapak® 250 Y, and columns having random packings. Also useful, however, are trickle towers and spray towers, and also rotary columns, pan scrubbers, cross-spray scrubbers and rotary scrubbers. Suitable gases are, for example, nitrogen or methane.

The absorbent stream 21 laden with C$_4$ hydrocarbons can be heated in a heat exchanger and then passed as stream 25 into a desorption column 26. In one process variant, the desorption step Dc) is performed by decompressing and/or heating the laden absorbent. The preferred process variant is the utilization of a vapor stream 24, which is supplied in the bottom of the desorption column 26.

The absorbent regenerated in the desorption stage is withdrawn as stream 27 from the desorption column 26 together with the condensed water. This biphasic mixture can be cooled in a heat exchanger and separated as stream 28 in a decanter 22 into an aqueous stream and an absorbent stream 29. The absorbent stream 29 is fed back to the absorber column 18, while the aqueous stream is evaporated in an evaporator and hence stream 24 is produced. Additionally or alternatively, additional water (stream 30) can also be evaporated in the evaporator. Low boilers present in the process gas stream, for example ethane or propane, and high-boiling components such as benzaldehyde, maleic anhydride and phthalic anhydride, can accumulate in the circulation stream. In order to limit the accumulation, a purge stream 23 can be drawn off.

The C$_4$ product gas stream 32 consisting essentially of n-butane, n-butenes and butadiene comprises generally 20% to 80% by volume of butadiene, 0% to 80% by volume of n-butane, 0% to 10% by volume of 1-butene and 0% to 50% by volume of 2-butenes, where the total amount is 100% by volume. In addition, small amounts of isobutane may be present.

A portion of the condensed top discharge from the desorption column comprising principally C$_4$ hydrocarbons is recycled as stream 35 into the top of the column, in order to increase the separation performance of the column.

The liquid (stream 33) or gaseous (stream 34) C$_4$ product streams leaving the condenser are subsequently separated by extractive distillation in step E) with a butadiene-selective solvent into a stream comprising butadiene and the selective solvent, and a stream comprising n-butenes.

The extractive distillation can be performed, for example, as described in "Erdöl and Kohle-Erdgas-Petrochemie", volume 34 (8), pages 343 to 346, or "Ullmanns Enzyklopädie der Technischen Chemie", volume 9, 4th edition 1975, pages 1 to 18. For this purpose, the C$_4$ product gas stream is contacted with an extractant, preferably an N-methylpyrrolidone (NMP)/water mixture, in an extraction zone. The extraction zone generally takes the form of a scrubbing column comprising trays, random packings or structured packings as internals. This generally has 30 to 70 theoretical plates, in order that a sufficiently good separating action is achieved. Preferably, the scrubbing column has a re-scrubbing zone in the top of the column. This re-scrubbing zone serves for recovery of the extractant present in the gas phase with the aid of a liquid hydrocarbon return stream, for which the top fraction is condensed beforehand. The mass ratio of extractant to $C_4$ product gas stream in the feed to the extraction zone is generally 10:1 to 20:1. The extractive distillation is preferably operated at a bottom temperature in the range from 100 to 250° C., especially at a temperature in the range from 110 to 210° C., a top temperature in the range from 10 to 100° C., especially in the range from 20 to 70° C., and a pressure in the range from 1 to 15 bar, especially in the range from 3 to 8 bar. The extractive distillation column has preferably 5 to 70 theoretical plates.

Suitable extractants are butyrolactone, nitriles such as acetonitrile, propionitrile, methoxypropionitrile, ketones such as acetone, furfural, N-alkyl-substituted lower aliphatic acid amides such as dimethylformamide, diethylformamide, dimethylacetamide, diethylacetamide, N-formylmorpholine, N-alkyl-substituted cyclic acid amides (lactams) such as N-alkylpyrrolidones, especially N-methylpyrrolidone (NMP). In general, alkyl-substituted lower aliphatic acid amides or N-alkyl-substituted cyclic acid amides are used. Particularly advantageous are dimethylformamide, acetonitrile, furfural and especially NMP.

However, it is also possible to use mixtures of these extractants with one another, for example of NMP and acetonitrile, mixtures of these extractants with co-solvents and/or tert-butyl ethers, e.g. methyl tert-butyl ether, ethyl tert-butyl ether, propyl tert-butyl ether, n- or isobutyl tert-butyl ether. NMP is particularly suitable, preferably in aqueous solution, preferably with 0 to 20% by weight of water, more preferably with 7 to 10% by weight of water, especially with 8.3% by weight of water.

The top product stream from the extractive distillation column comprises essentially butane and butenes and small amounts of butadiene and is drawn off in gaseous or liquid form. In general, the stream consisting essentially of n-butane and 2-butene comprises up to 100% by volume of n-butane, 0% to 50% by volume of 2-butene, and 0% to 3% by volume of further constituents such as isobutane, isobutene, propane, propene and $C_5^+$ hydrocarbons.

The stream consisting essentially of n-butane and 2-butene can be fed fully or partly into the $C_4$ feed of the ODH reactor. Since the butene isomers in this recycle stream consist essentially of 2-butenes, and 2-butenes are generally oxidatively dehydrogenated more slowly to butadiene than 1-butene, this recycle stream can be catalytically isomerized before being fed into the ODH reactor. As a result, it is possible to adjust the isomer distribution in accordance with the isomer distribution present at thermodynamic equilibrium.

In a step F), the stream comprising butadiene and the selective solvent is distillatively separated into a stream consisting essentially of the selective solvent and a stream comprising butadiene.

The stream obtained at the bottom of the extractive distillation column generally comprises the extractant, water, butadiene and small proportions of butenes and butane and is fed to a distillation column. Butadiene can be obtained therein overhead or as a side draw. At the bottom of the distillation column, a stream comprising extractant, with or without water, is obtained, the composition of the stream comprising extractant and water corresponding to the composition as added to the extraction. The stream comprising extractant and water is preferably passed back into the extractive distillation.

If the butadiene is obtained via a side draw, the extraction solution thus drawn off is transferred into a desorption zone, and the butadiene is once again desorbed and re-scrubbed out of the extraction solution. The desorption zone may be configured, for example, in the form of a scrubbing column having 2 to 30 and preferably 5 to 20 theoretical plates, and optionally a re-scrubbing zone having, for example, 4 theoretical plates. This re-scrubbing zone serves for recovery of the extractant present in the gas phase with the aid of a liquid hydrocarbon return stream, for which the top fraction is condensed beforehand. As internals, structured packings, trays or random packings are provided. The distillation is preferably performed at a bottom temperature in the range from 100 to 300° C., especially in the range from 150 to 200° C., and a top temperature in the range from 0 to 70° C., especially in the range from 10 to 50° C. The pressure in the distillation column is preferably in the range from 1 to 10 bar. In general, a reduced pressure and/or an elevated temperature exist in the desorption zone compared to the extraction zone.

The product of value stream obtained at the top of the column comprises generally 90 to 100% by volume of butadiene, 0 to 10% by volume of 2-butene and 0 to 10% by volume of n-butane and isobutane. For further purification of the butadiene, a further distillation can be performed in accordance with the prior art.

Figure 6:
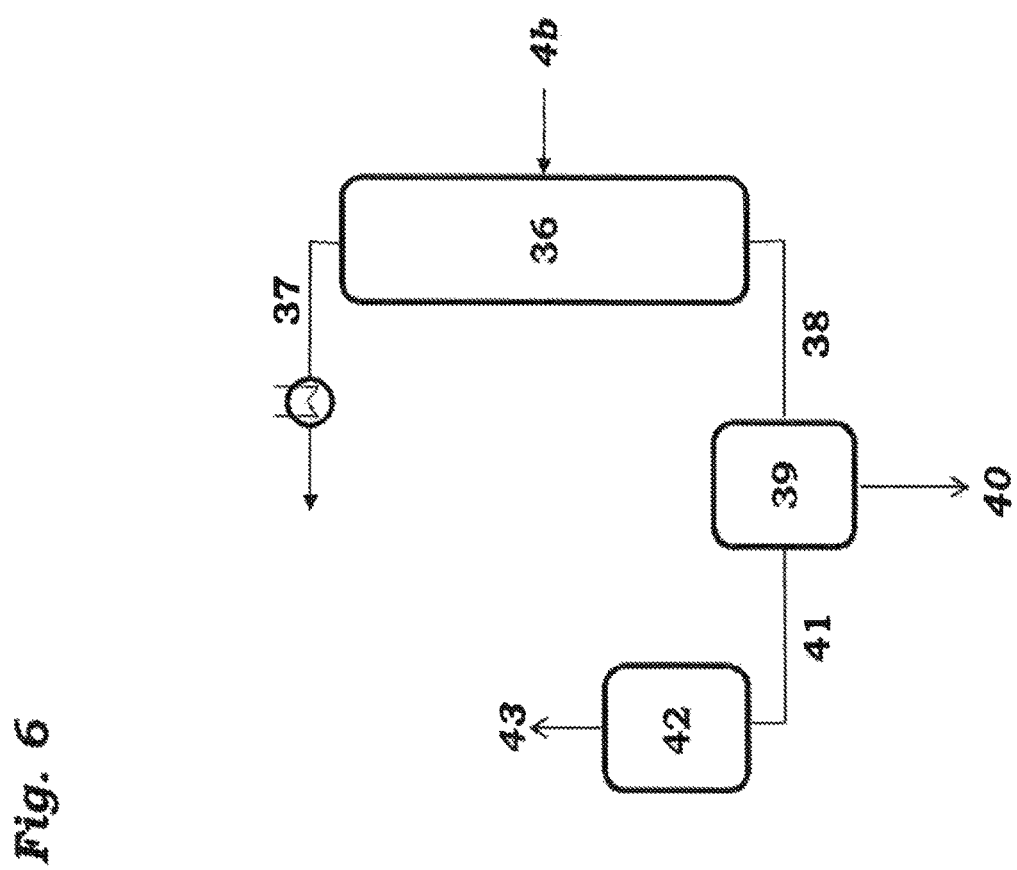
FIG. 6 is a schematic diagram of the reaction process with work-up of aqueous purge stream.

FIG. 6 shows how the aqueous purge stream is worked up further in accordance with the invention. The aqueous purge stream 4b and/or the aqueous substream obtained from the purge stream 6b are fed to the dewatering unit 36, a distillation column or an evaporator. This gives a stream 37 depleted of organic constituents and enriched in water, and a stream 38 enriched in organic constituents and depleted of water. The dewatering can be effected in a desired suitable dewatering unit known to those skilled in the art, for instance in a distillation column or in an evaporator, for example a falling-film evaporator, a thin-film evaporator or another evaporator known to those skilled in the art (for example of the Sambay type or of the Luwa type with rotating internals). The dewatering can optionally be improved by addition of entraining agents, for example an aromatic solvent. The entraining agent can then be removed from the water-enriched stream 37 after cooling and condensation. The temperature and pressure are not restricted any further. Typical temperatures are 30-200° C., preferably 40-150° C., more preferably 60-140° C. Typical pressures are 50 to 1500 mbar absolute, preferably 100 to 900 mbar absolute. The dewatering can be accomplished in one or more stages. Typically, the water content of the water-depleted stream 38 is below 10% by weight. One or more products of value 40 can be removed from the stream 38 in a removal unit 39. For example, maleic anhydride can be obtained as product of value according to the prior art (see, for example, U.S. Pat. Nos. 3,965,126, 4,219,388, 4,961,827 or PERP Report 2013 May "Maleic Anhydride" from Nexant, published in December 2013). In this case, the removal unit may comprise, for example, a further evaporator, heat exchanger and a distillation column. In the first evaporator, residues of water are evaporated and a portion of the maleic acid is dehydrated to maleic anhydride and evaporated. This leaves the residual portion of the maleic acid and of the maleic anhydride and further high-boiling by-products as residue. The gaseous stream from the evaporator is cooled, optionally by means of several heat exchanger stages. In the distillation column, maleic anhydride can be obtained in the side draw, while low boilers are obtained via the top. Substances obtained in the bottoms can be returned to the evaporator. Low boilers and residue from the evaporator can be fed as stream 41, forming an offgas 43 for thermal utilization, to an incineration furnace 42. The thermal energy obtained can be at least partly recycled into the process.

EXAMPLES

Dehydrogenation Experiments

Dehydrogenation experiments were conducted in a Miniplant reactor. The Miniplant reactor was a salt bath reactor having a length of 500 cm and an internal diameter of 29.7 mm, and a thermowell having an external diameter of 6 mm. On a catalyst support rested a 10 cm-long downstream bed consisting of 60 g of steatite rings of geometry 7 mm×7 mm×4 mm (external diameter×length×internal diameter). This was followed by 2705 g of an undiluted eggshell catalyst (active composition content 19.6% by weight; bed height 384 cm, bed volume in the reactor 2552 ml) in the form of hollow cylinders of dimensions 7 mm×3 mm×4 mm (external diameter×length×internal diameter). The catalyst bed was adjoined by an 85 cm-long upstream bed consisting of 494 g of steatite rings of geometry 7 mm×7 mm×4 mm (external diameter×length×internal diameter).

The temperature of the reaction tube was controlled over its entire length with a salt bath which flowed around it. The reaction gas mixture used was a mixture comprising a total of 8% by volume of 1-, cis-2- and trans-2-butenes, small amounts of i-butene, 2% by volume of butanes (n- and isobutane), 12% by volume of oxygen, 5% by volume of water and remainder of nitrogen. The space velocity through the reaction tube was 5500 l (STP)/h of total gas. The temperature of the salt after the startup, during stable operation, was 374° C. The conversion of butenes was 85%, and the selectivity for butadiene was likewise about 85%. Secondary components detected comprise acetic acid, methacrolein, methyl vinyl ketone, methyl ethyl ketone, crotonaldehyde, acrylic acid, propionic acid, methacrylic acid, vinylcyclohexane, maleic anhydride, ethylbenzene, styrene, furanone, benzaldehyde, benzoic acid, phthalic anhydride, fluorenone, anthraquinone, formaldehyde, carbon monoxide and carbon dioxide.

The ODH offgas was cooled to 200° C. by means of a heat exchanger. It can be run directly to a flare or introduced from above into the top of a quench column. The quench column is 920 mm in length and has an internal diameter of 56 mm. After 300 mm and after 610 mm, Venturi nozzles having a central hole diameter of 8 mm are installed. The coolant is supplied from above to the top of the quench through two full-cone nozzles on either side of the gas inlet tube (smallest free cross section 1.15 mm). The gas/coolant mixture passes through the quench column via the two Venturi nozzles and is collected at the bottom of the quench column, and two quench circulation streams are conveyed with the aid of two pumps through a heat exchanger back to the top of the column. The pressure is measured on the pressure side of the pumps. A portion of the laden coolant can be withdrawn from the circulation stream. In addition, coolant (water and/or mesitylene) can be fed to the circulation stream.

The product gas is sent to further workup.

Example 1

1111 g/h of deionized water and 2584 g/h of mesitylene (1,3,5-trimethylbenzene) are supplied to the circulation stream of coolant around the quench column. The two circulation flow rates around the quench column are 60 l/h. The coolant level in the column bottom is kept constant by discharging coolant from the circulation system.

When the reactor has attained a stable state, the reactor offgas is diverted from the flare into the quench column. After a few hours, the coolant just upstream of one cone nozzle has a temperature of 75° C. and just upstream of the second cone nozzle has a temperature of 76° C., and in the column bottom has a temperature of 72° C. The temperature in the gas space above the liquid coolant is measured at 74° C. The pressure in the coolant circuit is 1.5 bar gauge. The content of water vapor and mesitylene in the gas which enters and leaves the quench column is measured by online GC. 709 g/h of laden coolant are discharged as purge stream. The total inventory of coolant in the quench column is 3000 g. The phase ratio in the quench circuit and in the purge stream, expressed as mass of water to mass of mesitylene, is 0.43. The reactor and quench ran for more than 2400 hours with a virtually constant coolant circulation flow rate, without any significant changes in the pressures upstream of the cone nozzles.

After operation for 10 days, a sample was taken from the coolant circuit. The aqueous fraction of the coolant was removed. At a sample pH of 2.6, the total organic carbon content was 4.4% by weight. The water content, determined via Karl Fischer titration, was 90.3% by weight. By means of capillary electrophoresis, 0.58% by weight of phthalic acid, 6.4% by weight of maleic acid, 0.18% by weight of benzoic acid, 0.43% by weight of acrylic acid and 0.44% by weight of acetic acid were found.

The calorific value of the sample was about 1050 kJ/kg.

Example 2

1112 g/h of deionized water and 2173 g/h of mesitylene (1,3,5-trimethylbenzene) are fed to the circulation stream of coolant around the quench column (see table). The circulation flow rate around the quench column in each case is 60 l/h through 2 full-cone nozzles. The coolant level in the bottom is kept constant by discharging coolant from the circuit.

When the reactor has reached a steady state, the reactor offgas is diverted from the flare into the quench column. After a few hours, the coolant just upstream of the cone nozzle has reached a temperature of 75° C., and a temperature in the bottom of 73° C. The temperature of the gas space above the coolant level is measured at 75° C. The pressure in the coolant circuit is 1.5 bar gauge. The content of water vapor and mesitylene in the product gas which leaves the quench column is measured by online GC. The phase ratio in the quench circuit, expressed as the mass of water relative to the mass of mesitylene, is 0.53. The reactor and quench ran for more than 150 hours with a virtually constant coolant circulation flow rate, without any significant changes in the pressure.

Example 3

1314 g/h of deionized water and 2083 g/h of mesitylene (1,3,5-trimethylbenzene) are fed to the circulation stream of coolant around the quench column (see table). The circulation flow rate around the quench column in each case 60 l/h through 2 full-cone nozzles. The coolant level in the bottom is kept constant by discharging coolant from the circuit.

When the reactor has reached a steady state, the reactor offgas is diverted from the flare into the quench column.

After a few hours, the coolant just upstream of the cone nozzle has reached a temperature of 75° C., and a temperature in the bottom of 73° C. The temperature of the gas space above the coolant level is measured at 75° C. The pressure in the coolant circuit is 1.5 bar gauge. The content of water vapor and mesitylene in the product gas which leaves the quench column is measured by online GC. The phase ratio in the quench circuit, expressed as the mass of water relative to the mass of mesitylene, is 0.99. The reactor and quench ran for more than 150 hours with a virtually constant coolant circulation flow rate, without any significant changes in the pressure.

Example 4

1111 g/h of deionized water and 1730 g/h of mesitylene (1,3,5-trimethylbenzene) are fed to the circulation stream of coolant around the quench column (see table). The circulation flow rate around the quench column in each case is 60 l/h through 2 full-cone nozzles. The coolant level in the bottom is kept constant by discharging coolant from the circuit.

When the reactor has reached a steady state, the reactor offgas is diverted from the flare into the quench column. After a few hours, the coolant just upstream of the cone nozzle has reached a temperature of 75° C., and a temperature in the bottom of 73° C. The temperature of the gas space above the coolant level is measured at 75° C. The pressure in the coolant circuit is 1.5 bar gauge. The content of water vapor and mesitylene in the product gas which leaves the quench column is measured by online GC. The phase ratio in the quench circuit, expressed as the mass of water relative to the mass of mesitylene, is 0.84. The reactor and quench ran for more than 330 hours with a virtually constant coolant circulation flow rate, without any significant changes in the pressure.

After 1 day of operation, a sample was taken from the coolant circuit. The aqueous fraction of the coolant was removed. At a pH of the sample of 2.6, the total content of organic carbon was 3.0% by weight. By means of capillary electrophoresis, 0.40% by weight of phthalic acid, 3.7% by weight of maleic acid, 0.06% by weight of benzoic acid, 0.34% by weight of acrylic acid and 0.51% by weight of acetic acid were found.

Example 5

1465 g/h of deionized water and 1730 g/h of mesitylene (1,3,5-trimethylbenzene) are fed to the circulation stream of coolant around the quench column (see table). The circulation flow rate around the quench column in each case 60 l/h through 2 full-cone nozzles. The coolant level in the bottom is kept constant by discharging coolant from the circuit.

When the reactor has reached a steady state, the reactor offgas is diverted from the flare into the quench column. After a few hours, the coolant just upstream of the cone nozzle has reached a temperature of 75° C., and a temperature in the bottom of 73° C. The temperature of the gas space above the coolant level is measured at 75° C. The pressure in the coolant circuit is 1.5 bar gauge. The content of water vapor and mesitylene in the product gas which leaves the quench column is measured by online GC. The phase ratio in the quench circuit, expressed as the mass of water relative to the mass of mesitylene, is 0.99. The reactor and quench ran for more than 330 hours with a virtually constant coolant circulation flow rate, without any significant changes in the pressure.

After 14 days of operation, a sample was taken from the coolant circuit. The aqueous fraction of the coolant was removed. At a pH of the sample of 2.9, the total content of organic carbon was 1.7% by weight. By means of capillary electrophoresis, 0.17% by weight of phthalic acid, 1.7% by weight of maleic acid, 0.05% by weight of benzoic acid, 0.31% by weight of acrylic acid and 0.34% by weight of acetic acid were found.

|  | Example 1 | Example 2 | Example 3 | Example 4 | Example 5 |
|---|---|---|---|---|---|
| Feed of water vapor from reactor [g/h] | 613 | 587 | 629 | 593 | 585 |
| Feed of water to the circulation stream [g/h] | 1111 | 1112 | 1314 | 1111 | 1465 |
| Removal of water from circulation stream [g/h] | −214 | −302 | −525 | −490 | −916 |
| Feed of of mesitylene to the circulation stream [g/h] | 1911 | 2173 | 2083 | 1730 | 1730 |
| Removal of mesitylene from circulation stream [g/h] | −495 | −574 | −530 | −583 | −586 |
| Phase ratio in the circulation stream [$g_{water}/g_{mesitylene}$] | 0.43 | 0.53 | 0.99 | 0.84 | 1.56 |

The invention claimed is:

1. A process for preparing butadiene from n-butenes, comprising the steps of:

A) providing an input gas stream comprising n-butenes;

B) feeding the input gas stream and a gas that includes oxygen into at least one oxidative dehydrogenation zone to oxidatively dehydrogenate the n-butenes to butadiene, and providing a product gas stream comprising butadiene, unconverted n-butenes, water vapor, oxygen, low-boiling hydrocarbons and high-boiling secondary components, with or without carbon oxides and with or without inert gases;

Ca) cooling the product gas stream b by contacting with a cooling medium in at least one cooling zone, the cooling medium being at least partly recycled and having an aqueous phase and an organic phase that includes an organic solvent, wherein the organic solvent used in the step Ca) is selected from the group consisting of toluene, o-, m- and p-xylene, mesitylene, mono-, di- and triethylbenzene, mono-, di- and triisopropylbenzene and mixtures thereof, to produce a cooled product gas stream;

Cb) compressing the cooled product gas stream, which is optionally depleted of high-boiling secondary components in at least one compression stage to provide at least one aqueous condensate stream c1 and one gas stream c2 comprising butadiene, n-butenes, water vapor, oxygen and low-boiling hydrocarbons, with or without carbon oxides and with or without inert gases;

D) removing uncondensable and low-boiling gas constituents comprising oxygen and low-boiling hydrocarbons, with or without carbon oxides and with or without inert gases, as gas stream d2 from the gas stream c2 by absorbing $C_4$ hydrocarbons comprising butadiene and n-butenes in an absorbent to provide an absorbent stream laden with $C_4$ hydrocarbons and the gas stream d2, and then desorbing the $C_4$ hydrocarbons from the absorbent stream laden with $C_4$ hydrocarbons to provide a $C_4$ product gas stream d1;

E) separating the $C_4$ product stream d1 by extractive distillation with a butadiene-selective solvent into a stream e1 that includes butadiene and the butadiene-selective solvent, and a stream e2 comprising n-butenes;

F) distilling the stream e1 to provide a stream f1 consisting essentially of the butadiene-selective solvent and a stream f2 that includes butadiene;

G) removing a portion of the aqueous phase of the cooling medium which circulates in step Ca) as aqueous purge stream g;

H) separating by distillation the aqueous purge stream g into a fraction h1 enriched in organic constituents and a fraction h2 depleted of organic constituents; and provide I) at least one fraction it as product of value from the fraction h1.

2. The process according to claim 1, where at least 90% by weight of the organic constituents present in the aqueous purge stream g are removed by distillation from the aqueous purge stream g.

3. The process according to claim 1, further comprising
J) separating at least one fraction j1 from the fraction hi.

4. The process according to claim 1, wherein, in the step I), maleic acid and/or maleic anhydride as product of value is/are obtained as fraction i1 from the fraction h1 by a distillation.

5. The process according to claim 3, wherein the fraction j1 is sent to an incineration and the heat which arises in the incineration is utilized for operation of a distillation column or of an evaporator in which the aqueous purge stream g is distilled.

6. The process according to claim 5, wherein the portion of the aqueous phase of the cooling medium which is removed in the step G) is such that the heat which arises in the incineration of fraction j1 is sufficient to operate the distillation column or the evaporator.

7. The process according to claim 6, wherein the portion of the aqueous phase of the cooling medium which is removed in the step G) is 0.5% to 100% of the mass flow of the butenes supplied to the oxidative dehydrogenation zone.

8. The process according to claim 1, wherein the cooling medium is fed into the cooling zones through one or more nozzles.

9. The process according to claim 8, wherein a flow is generated in the nozzle(s), in which the Reynolds number Re of the cooling medium is at least 100.

10. The process according to claim 1, wherein a volume-specific power input into the cooling medium is at least $10^3$ W/m$^3$.

11. The process according to claim 1, wherein a coefficient of variation for each component of the cooling medium on entry into the cooling zones is less than 1.

12. The process according to claim 1, wherein the step Cb) comprises at least one compression step Cba) and at least one cooling step Cbb).

13. The process according to claim 12, wherein the coolant in the cooling step Cbb) comprises the same organic solvent which is used in the step Ca) as the organic phase of the cooling medium.

14. The process according to claim 1, wherein the step Cb) comprises a plurality of compression step Cba1) to Cban) and cooling steps Cbb1) to Cbbn).

15. The process according to claim 1, wherein the step D) comprises steps Da) to Dc):
Da) absorbing the $C_4$ hydrocarbons comprising butadiene and n-butenes in a high-boiling absorbent, giving an absorbent stream laden with $C_4$ hydrocarbons and the gas stream d2,
Db) removing oxygen from the absorbent stream laden with $C_4$ hydrocarbons from the step Da) by stripping with an uncondensable gas stream, and
Dc) desorbing the $C_4$ hydrocarbons from the absorbent stream laden with $C_4$ hydrocarbons, giving a $C_4$ product gas stream d1 comprising less than 100 ppmw of oxygen.

16. The process according to claim 15, wherein the high-boiling absorbent used in the step Da) is an aromatic hydrocarbon solvent.

* * * * *